US011944067B2

(12) United States Patent
Strauss et al.

(10) Patent No.: US 11,944,067 B2
(45) Date of Patent: Apr. 2, 2024

(54) CAGE ASSEMBLY FOR ANIMAL TEST SUBJECTS

(71) Applicant: NOVOCURE GMBH, Root (CH)

(72) Inventors: Shalom Strauss, Haifa (IL); Yoram Wasserman, Haifa (IL); Shiri Davidi, Haifa (IL); Roni Blat, Haifa (IL); Golan Bar Tal, Haifa (IL); Moshe Giladi, Haifa (IL); Michael Krinitsky, Haifa (IL); Mijal Munster, Haifa (IL)

(73) Assignee: NOVOCURE GMBH, Root (CH)

( * ) Notice: Subject to any disclaimer, the term of this patent is extended or adjusted under 35 U.S.C. 154(b) by 0 days.

(21) Appl. No.: 17/958,827

(22) Filed: Oct. 3, 2022

(65) Prior Publication Data

US 2023/0023608 A1 Jan. 26, 2023

Related U.S. Application Data

(63) Continuation of application No. 17/127,180, filed on Dec. 18, 2020, now Pat. No. 11,464,203.

(60) Provisional application No. 63/104,788, filed on Oct. 23, 2020, provisional application No. 62/951,599, filed on Dec. 20, 2019.

(51) Int. Cl.
*A01K 1/03* (2006.01)
*A01K 1/00* (2006.01)

(52) U.S. Cl.
CPC ............ *A01K 1/031* (2013.01); *A01K 1/0047* (2013.01)

(58) Field of Classification Search
CPC ........ A01K 1/03; A01K 1/031; A01K 1/0047; A01K 1/0236; A01K 1/0245; A01K 1/032; A01K 1/033; A01K 1/034; A01K 31/002; B65D 25/04; B65D 25/08
See application file for complete search history.

(56) References Cited

U.S. PATENT DOCUMENTS

| | | | | | |
|---|---|---|---|---|---|
| 2,932,279 | A | * | 7/1958 | Giles | A01K 1/033 |
| 6,058,523 | A | * | 5/2000 | Sleboda | A47K 1/04 4/619 |
| 6,588,373 | B1 | * | 7/2003 | Strzempko | A01K 1/00 119/496 |
| 2014/0058214 | A1 | * | 2/2014 | Woodward | A01K 1/03 600/301 |
| 2017/0118947 | A1 | * | 5/2017 | Thoma | A01K 1/02 |

* cited by examiner

*Primary Examiner* — Joshua J Michener
*Assistant Examiner* — Henry Hooper Mudd
(74) *Attorney, Agent, or Firm* — Ballard Spahr LLP

(57) ABSTRACT

A cage assembly can have at least one enclosure. Each enclosure can have a floor defining a floor area having a major dimension and a cover having a bottom surface. A spacing between the bottom surface of the cover and the floor can define a cage height. At least one sidewall can extend between the floor and the cover. A ratio of the cage height to the major dimension of the floor area of each enclosure of the at least one enclosure can be at least 0.70.

20 Claims, 25 Drawing Sheets

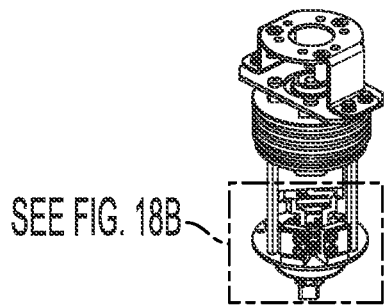
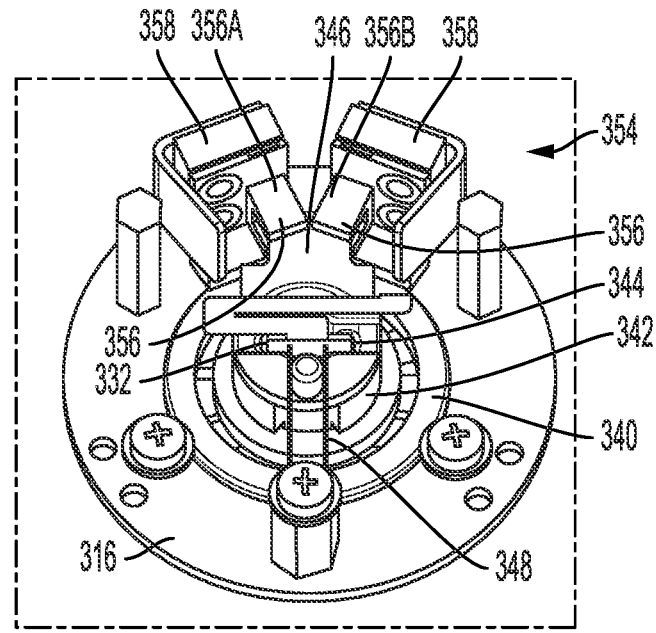
FIG. 18A    FIG. 18B
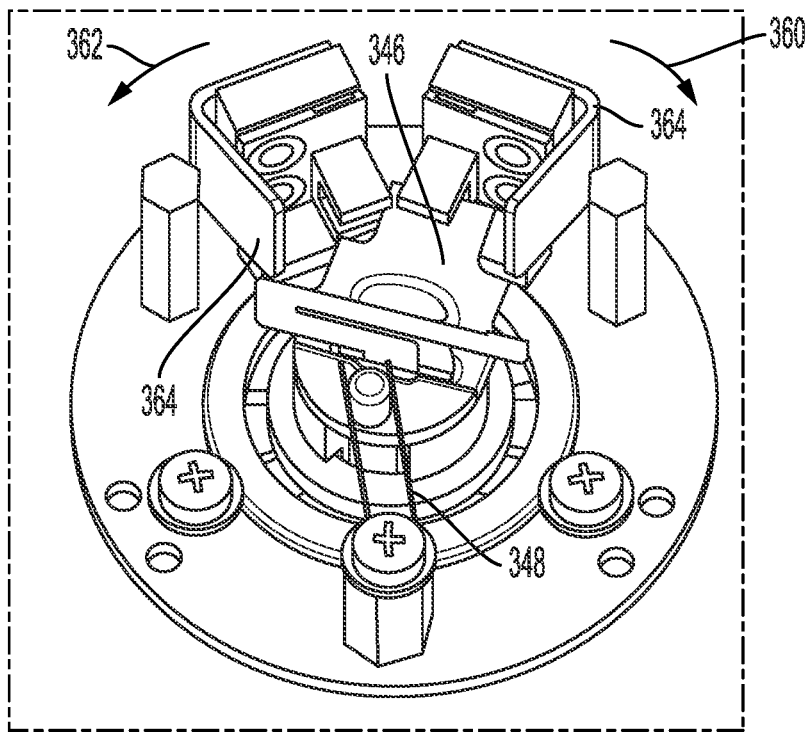
FIG. 19

CAGE ASSEMBLY FOR ANIMAL TEST SUBJECTS

CROSS-REFERENCE TO RELATED APPLICATIONS

The application is a continuation of U.S. patent application Ser. No. 17/127,180, filed Dec. 18, 2020, which claims priority to and the benefit of the filing date of U.S. Provisional Patent Application No. 62/951,599, filed Dec. 20, 2019, and U.S. Provisional Patent Application No. 63/104,788, filed Oct. 23, 2020. The entirety of each of the above-identified applications is hereby incorporated by reference herein.

FIELD

The invention relates to systems, apparatuses, and methods for testing and using tumor treating fields (TTFields). The disclosure includes descriptions of cage assemblies, treatment assemblies, and swivel systems for use with animal test subjects.

BACKGROUND

Tumor Treating Fields, or TTFields, are low intensity (e.g., 1-3 V/cm) alternating electric fields within the intermediate frequency range (100-300 kHz). This non-invasive treatment targets solid tumors and is described in U.S. Pat. No. 7,565,205, which is hereby incorporated herein by reference in its entirety. TTFields disrupt cell division through physical interactions with key molecules during mitosis. TTFields therapy is an approved mono-treatment for recurrent glioblastoma, and an approved combination therapy with chemotherapy for newly diagnosed patients. These electric fields are induced non-invasively by transducer arrays (i.e., arrays of electrodes) placed directly on the patient's scalp. TTFields also appear to be beneficial for treating tumors in other parts of the body. Laboratory research has begun to test intermediate frequency alternating electric fields (Tumor Treating Fields, or TTFields) to subcutaneous tumors and orthotropic tumors located in the torso of small animals (e.g., mice).

SUMMARY

Described herein, in various aspects, is a cage assembly for animal test subjects. Optionally, the cage assembly can be used to house one or more animal test subjects that are undergoing TTFields or control treatments.

A cage assembly can comprise at least one enclosure. Each enclosure can have a floor defining a floor area having a major dimension and a cover having a bottom surface. A spacing between the bottom surface of the cover and the floor can define a cage height. At least one sidewall can extend between the floor and the cover. A ratio of the cage height to the major dimension of the floor area of each enclosure of the at least one enclosure can be at least 0.70.

The at least one enclosure can comprise first and second enclosures.

The at least one enclosure can consist of first and second enclosures.

The first and second enclosures can share a common sidewall that separates the floor area of the first enclosure from the floor area of the second enclosure.

The common sidewall can defines at least one opening between the first enclosure and the second enclosure.

Each of the first and second enclosures can comprise a respective shelter subassembly that extends inwardly from the common sidewall within the enclosure. The shelter subassembly can at least partially surround the opening within the common sidewall.

The floor of each enclosure can define corners, each corner of the floor of the enclosure having a radius of at least 17 mm.

The major dimension of the floor area of each enclosure can be no greater than 250 mm.

The floors of the first and second enclosures can be unitarily constructed.

The covers of the first and second enclosures can be unitarily constructed as a cover assembly.

The cover assembly can comprise first and second openings that provide communication, respectively, with the first and second enclosures. The first opening can be configured provide communication for a first cable, and the second opening can be configured provide communication for a second cable.

The cover assembly can comprise first and second swivel assemblies positioned in overlying relation, respectively, to the first and second openings. The first swivel assembly can be configured to receive a proximal portion of the first cable, and the second swivel assembly can be configured to receive a proximal portion of the second cable.

Each of the first swivel assembly and the second swivel assembly can comprise a motor housing and a motor received within the motor housing. The motor of the first swivel assembly can be configured to be coupled to a first cable to permit adjustment of the first cable. The motor of the second swivel assembly can be configured to be coupled to a second cable to permit adjustment of the second cable.

The at least one enclosure can comprise a first enclosure. The cover can comprise a swivel assembly positioned in overlying relation to the first enclosure. The cover can further comprise an opening that provides communication with the first enclosure. The opening can be configured to provide communication between the cable and the swivel assembly.

The swivel assembly can comprise a motor. The motor can be configured to be coupled to a proximal portion of the cable to permit adjustment of movement of the cable.

The at least one sidewall of each of the first and second enclosures can further comprise a front sidewall, a rear sidewall, and a transverse sidewall opposing the common sidewall and extending between the front sidewall and the rear sidewall.

At least a portion of the front sidewalls of the first and second enclosures can be unitarily constructed.

The rear sidewalls of the first and second enclosures can be unitarily constructed.

The front sidewalls of the first and second enclosures can comprise a base portion that is secured to the transverse sidewalls of the first and second enclosures and a door that is pivotably coupled to the base portion. The door can be configured for movement about and between a closed position in which the door cooperates with the front, transverse, and rear sidewalls and the covers of the first and second enclosures to enclose an interior space within the cage assembly and an open position in which the interior space of the cage assembly is accessible.

The door can be pivotably coupled to the base portion by a hinged connection.

The cage assembly can further comprise a latch that is mechanically coupled to the door. The latch can be moveable about and between a latched position that prevents pivotal movement of the door when the door is in the closed position and an unlatched position that permits pivotal movement of the door relative to the base portion.

The floor, the cover, and the at least one sidewall of each enclosure can comprise polycarbonate.

At least a portion of the cover and the at least one sidewall of each enclosure can be transparent.

The cover can define an opening that is configured to receive an electrical cord.

The floor of each enclosure can comprise padding.

At least one sidewall of each enclosure can comprise ventilation openings.

The cage assembly can further comprise at least one filter that is configured to overlie at least one ventilation opening of the at least one sidewall.

The cage assembly can further comprise a frame that is configured to mechanically couple the filter to the at least one sidewall.

The cage assembly can be sealed so that all or substantially all ventilation to each enclosure travels through the at least one filter before entering a ventilation opening.

The sidewalls of each enclosure can have equal lengths.

The ratio of the cage height to the major dimension of the floor area of each enclosure of the at least one enclosure can be at least 1.0.

A cage assembly can comprise at least one enclosure. Each enclosure can have a floor defining a floor area having a major dimension and a cover having a bottom surface. A spacing between the bottom surface of the cover and the floor can define a cage height. At least one sidewall can extend between the floor and the cover. The height, h, can be a function of the major dimension, Y, of the floor according to the formula: $h \geq (Y^2 - 6400)/320$, where h and Y are in millimeters.

A method can comprise positioning an animal subject within each enclosure of the cage assembly and coupling a distal end of a cable to the animal subject within each enclosure. At least 90% of the floor area of the enclosure can be accessible by the animal subject.

The method can further comprise coupling a proximal end of each cable to a swivel assembly. Each cable can have an operative portion having an operative length. Each operative length can be selected so that each test subject can be at no position within a respective enclosure at which a spacing between the operative portion of the cable is within a threshold distance of the floor.

The animal subject can be a mouse.

The cage assembly can comprise first and second enclosures. A first mouse can be positioned within the first enclosure. A second mouse can be positioned within the second enclosure.

The first and second enclosures can share a common sidewall that separates the floor area of the first enclosure from the floor area of the second enclosure. The common sidewall can define at least one opening between the first enclosure and the second enclosure. The at least one opening can permit communication between the first mouse and the second mouse.

The electrical cord can be coupled to the animal subject through a treatment assembly comprising a transducer array.

The method can further comprise using the electrical cord and the treatment assembly to apply an electric field to the animal subject within at least one enclosure.

The animal subject can have a tumor, and the electric field can be a tumor-treating field.

The method can further comprise inspecting or accessing the animal subject through the cage assembly without removing the animal subject from the cage assembly.

The method can further comprise removing the animal subject from the cage assembly and autoclaving the floor, the cover, and the at least one sidewall of each enclosure.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein:

FIG. 18A is a perspective view of the swivel of FIG. 12B.

FIG. 18B is a detail perspective view of a portion of the swivel of FIG. 18A, illustrating a torque sensor assembly having a pivot body in a neutral position.

FIG. 19 is a perspective view of the portion of the swivel as in FIG. 18B, illustrating the pivot body being rotated from the neutral position.

DETAILED DESCRIPTION

Figure 1:
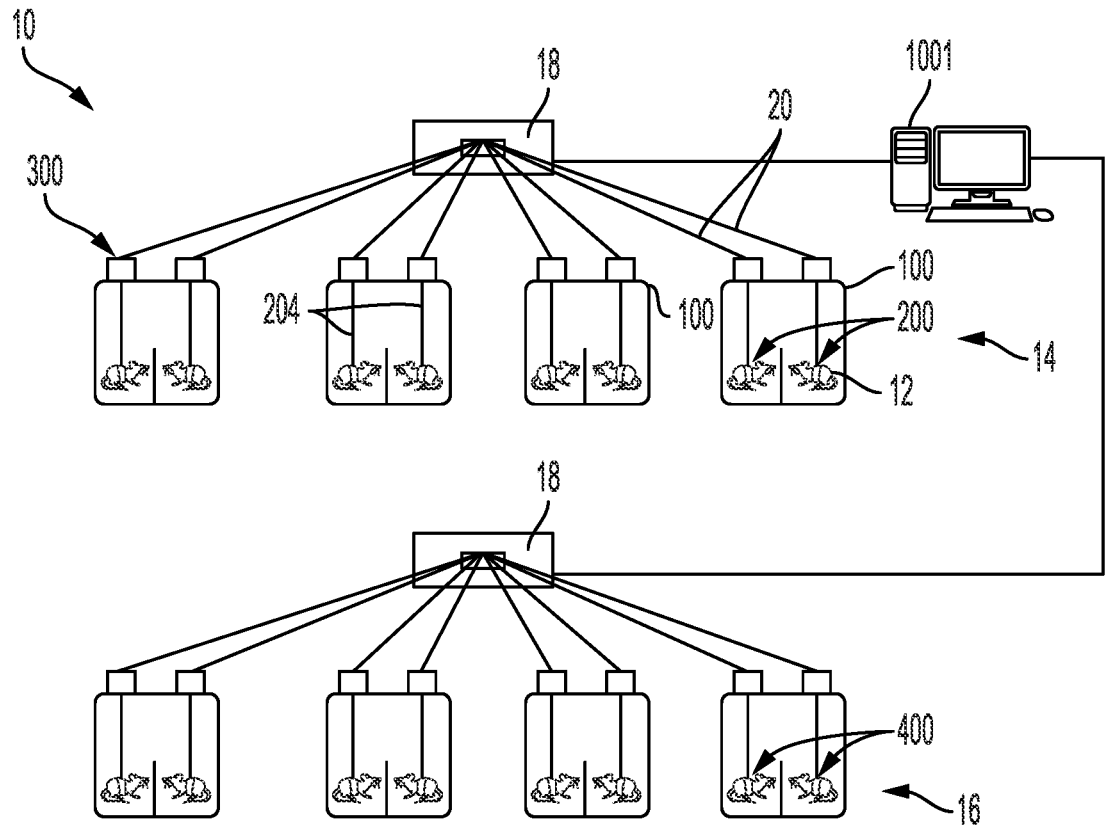
FIG. 1 is a system for testing TTField treatment in accordance with embodiments disclosed herein.
Figure 2:
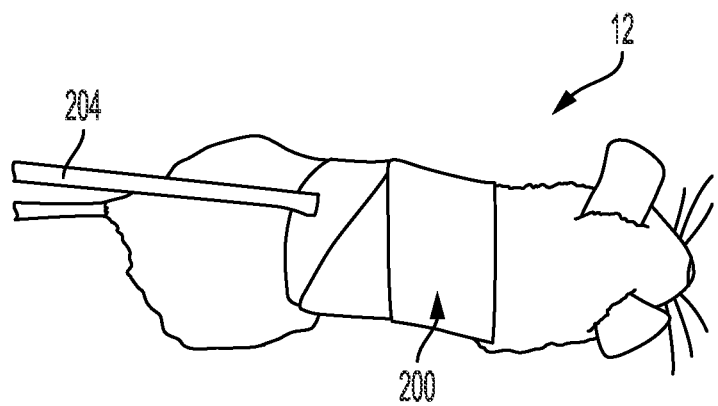
FIG. 2 is a test subject with a treatment assembly attached thereto.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "an electrode" can refer to one or more of such electrodes, and so forth.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of" For example, "at least one of A, B and C" explicitly includes only A, only B, only C, and combinations of each.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," it is contemplated that values within up to 15%, up to 10%, up to 5%, or up to 1% (above or below) of the particularly stated value can be included within the scope of those aspects. Similarly, use of "substantially" (e.g., "substantially parallel") or "generally" (e.g., "generally planar") should be understood to include embodiments in which angles are within about ten degrees, or within five degrees, or within one degree.

The word "or" as used herein means any one member of a particular list and also includes any combination of members of that list.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

In the following description and claims, wherever the word "comprise" or "include" is used, it is understood that the words "comprise" and "include" can optionally be replaced with the words "consists essentially of" or "consists of" to form another embodiment.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

TTFields, also referred to herein as alternating electric fields, are established as an anti-mitotic cancer treatment modality because they interfere with proper micro-tubule assembly during metaphase and eventually destroy the cells during telophase and cytokinesis. The efficacy increases with increasing field strength and the optimal frequency is cancer cell line dependent with 200 kHz being the frequency for which inhibition of glioma cells growth caused by TTFields is highest. For cancer treatment, non-invasive devices were developed with capacitively coupled transducers that are placed directly at the skin region close to the tumor. For patients with Glioblastoma Multiforme (GBM), the most common primary, malignant brain tumor in humans, the system for delivering TTFields therapy is called the OPTUNE™ system (Novocure Ltd.).

Because the effect of TTFields is directional with cells dividing parallel to the field affected more than cells dividing in other directions, and because cells divide in all directions, TTFields are typically delivered through two pairs of transducer arrays that generate perpendicular fields within the treated tumor. More specifically, for the OPTUNE system, one pair of electrodes is located to the left and right (LR) of the tumor, and the other pair of electrodes is located anterior and posterior (AP) to the tumor. Cycling the field between these two directions (i.e., LR and AP) ensures that a maximal range of cell orientations is targeted.

Although TTFields have been approved for use in certain patients, there is a need for systems that permit reliable, consistent, and safe testing of TTFields in animal test subjects. In small animal (e.g., mice) studies in which electrical components are coupled to the animals, the animals frequently chew or otherwise damage the electrical components. Additionally, when the animals are tethered using a cable, the animals frequently cause twisting of the cable. When too much slack is provided in such cables, the animals can easily turn over, leading to damage or incorrect positioning of the electrical components. When insufficient slack is provided in such cables, the movement of the animal can be too restricted. Further, it can be difficult to couple electrical components to animals without significant adjustment and repositioning.

Figure 24:
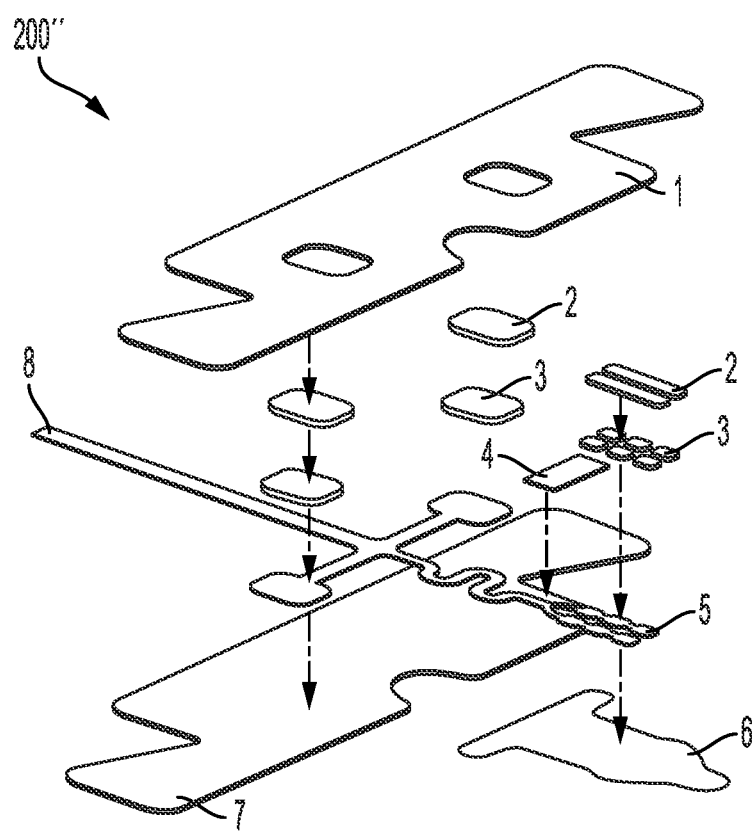
FIG. 24 is an exploded view of an exemplary treatment assembly.
Figure 25:
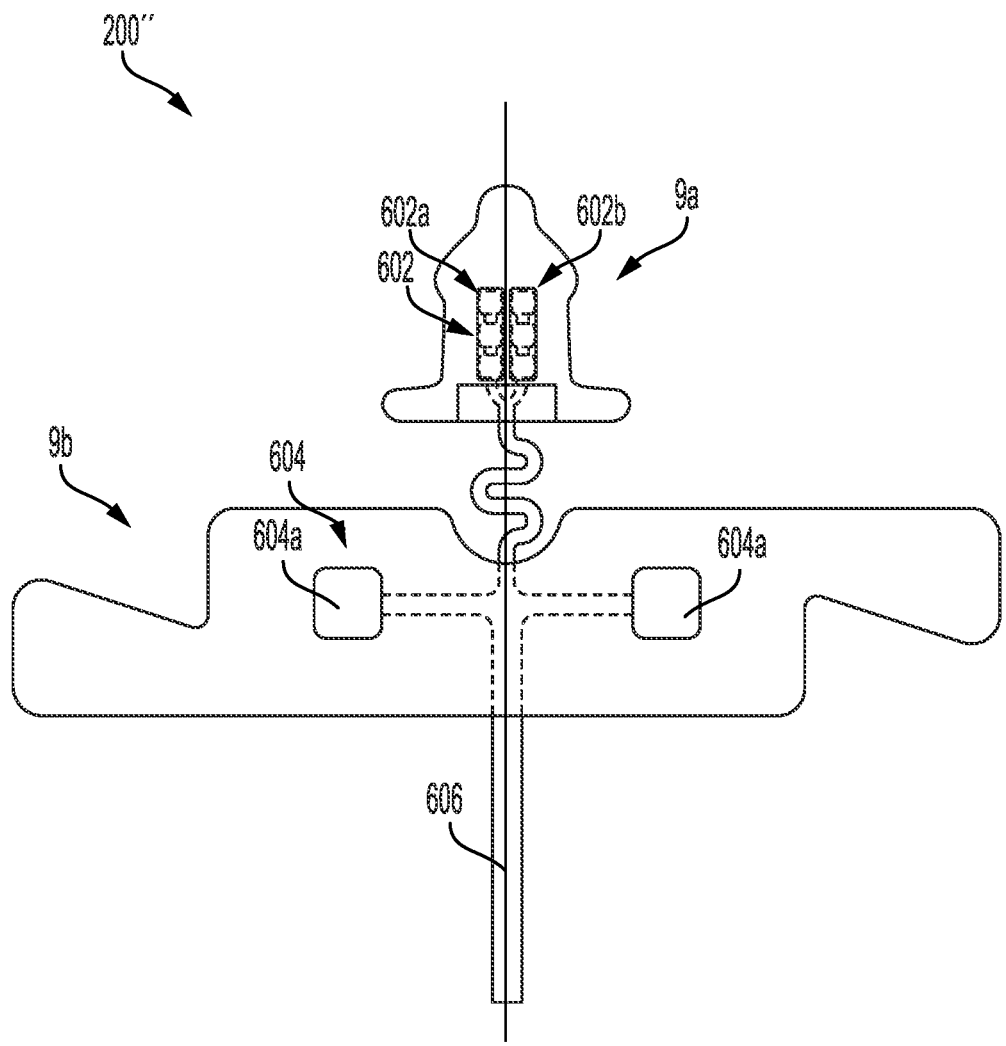
FIG. 25 is a top view of the exemplary treatment assembly as in FIG. 24.

Disclosed herein, in various aspects and with reference to FIG. 1, is a system 10 for providing TTFields to test subjects 12 (e.g., animal test subjects such as mice). The system 10 can comprise one or more cage assemblies 100 to receive and house one or more test subjects. Some test subjects in an experimental group 14 can be fitted with a TTField treatment assembly 200, 200', 200" (FIGS. 8, 9, and 24) that can comprise a transducer array for providing treatment to the test subjects. Other test subjects in a control group 16 can be fitted with a control heater treatment assembly 400,400' (FIGS. 10A-11B) that is configured to provide the same weight and heat as a TTField treatment assembly 200, 200', 200". A plurality of TTField treatment assemblies 200, 200', 200" can communicatively couple to a TTField generator 18. Optionally, the TTField generator can be a generator provided as part of an INOVITRO laboratory research system (NOVOCURE GMBH). Similarly, a plurality of control heater treatment assembly 400 can communicatively couple to the same or a separate TTField generator 18 (or other generator capable of initiating heat through the control heater treatment assembly as further disclosed herein). A computer 1001 can communicatively couple to the TTField generator 18. The computer 1001 can control the output of the TTField generator(s) 18 as well as log data from the TTField generator 18, the treatment assemblies 200, 200', 200", the control heater treatment assembly 400, and/or the test subjects 12.

Figure 8:
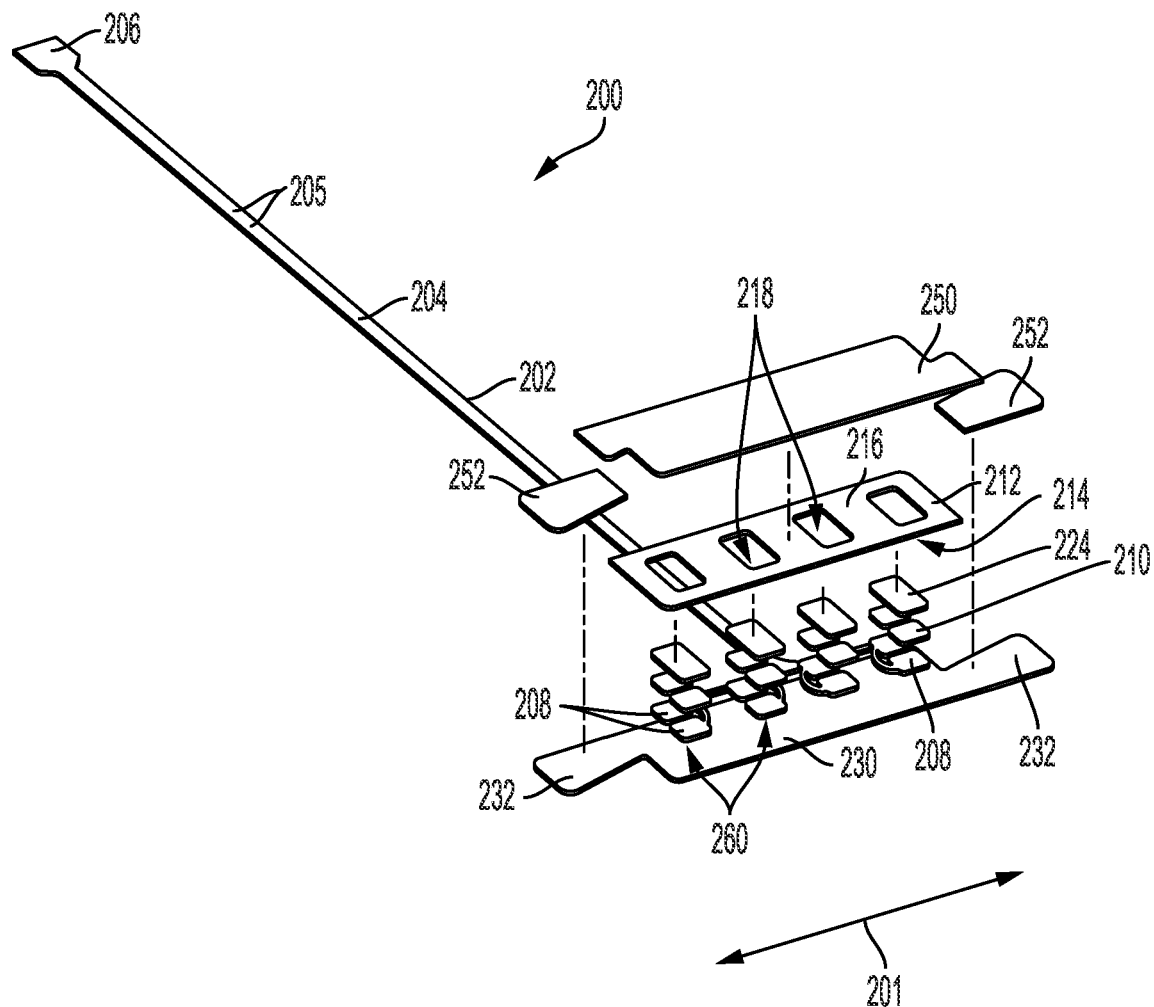
FIG. 8 is an exploded view of a treatment assembly, in accordance with embodiments disclosed herein, for use with the system as in FIG. 1.

The TTField treatment assemblies 200, 200', 200" and control heater treatment assemblies 400 can communicate with the TTField generator 18 via respective cables 204 (FIG. 8). To enable the test subject to move freely within the cage assembly 100 without winding the cable 204, the cable 204 can extend to, and couple to, a swivel 300 (also interchangeably referred to herein as a swivel assembly 300). The swivel 300 can, in turn, couple to a second cable 20 that extends to, and couples to, the TTField generator 18.

Thus, the swivel 300, as further disclosed herein, can enable electrical communication from the TTField generator 18, through the second cable 20, through the swivel assembly 300, and to the cable 204 for communicating with the treatment assemblies 200, 200', 200" while inhibiting winding of the cable 204.

The Cage Assembly

Figure 3:
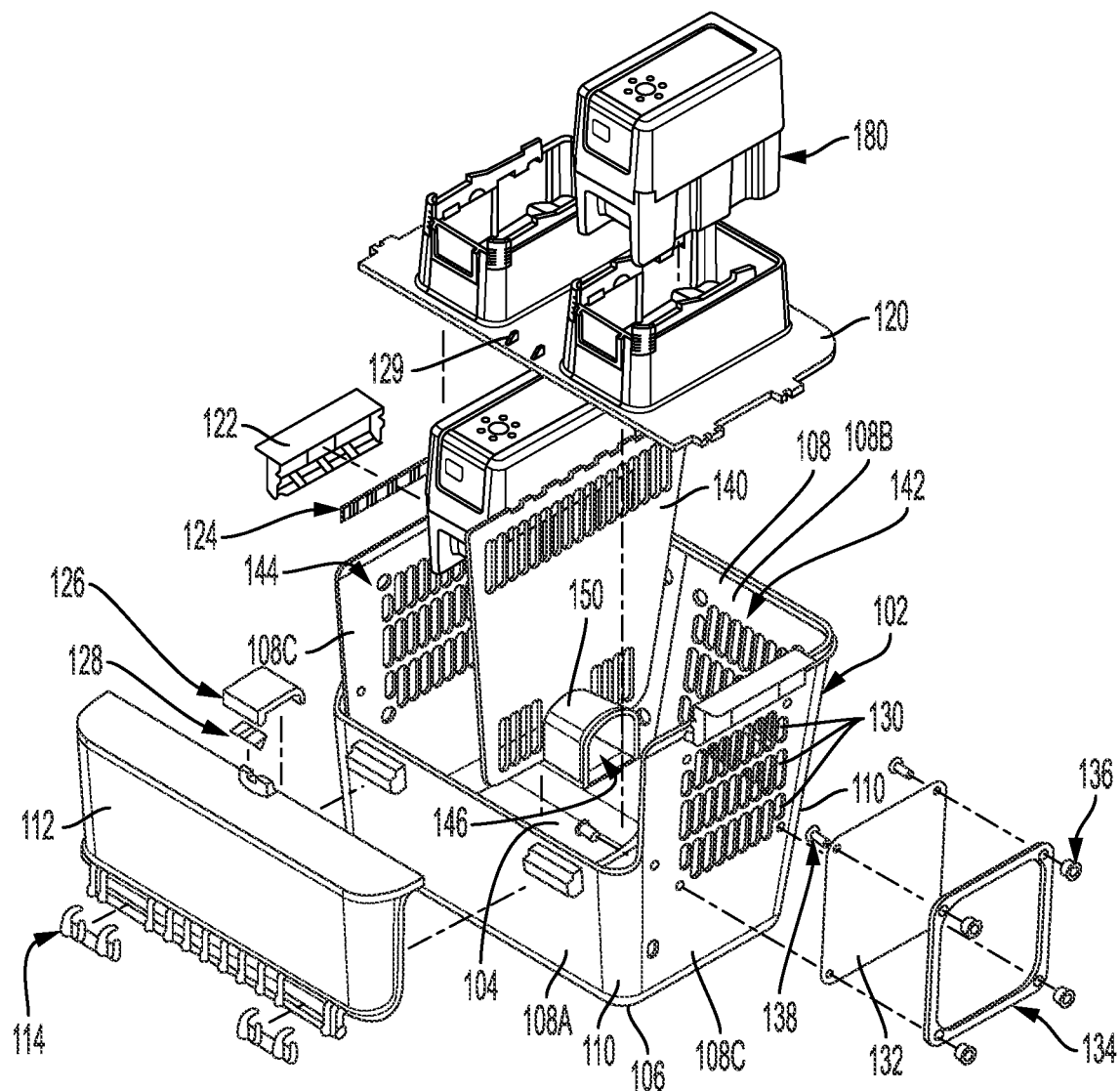
FIG. 3 is an exploded view of a cage system, in accordance with embodiments of the present disclosure.
Figure 4:
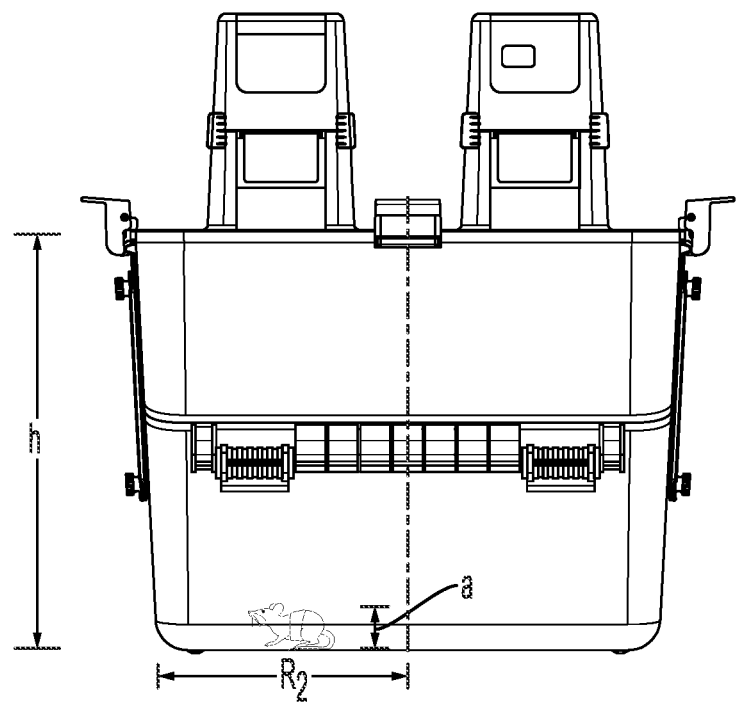
FIG. 4 is a front view of the cage system of FIG. 3.
Figure 5:
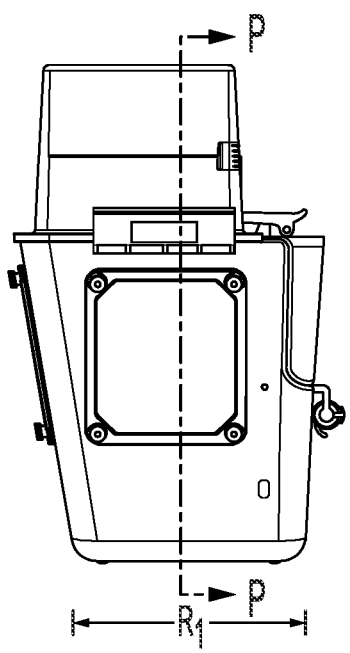
FIG. 5 is a side view of the cage system of FIG. 3.

Referring to FIGS. 3-5, the cage assembly 100 can include a main body 102. The main body 102 can comprise a floor 104 that defines a floor area having a major dimension. Optionally, the floor 104 can be rectangular or generally rectangular with corners 16. Optionally, the corners 16 can be rounded. The corners can have, for example, a radius of about 17 mm. The major dimension can be a maximum diagonal between the corners 106 of the cage. The main body 102 can further comprise one or more sidewalls 108. For example, the main body 102 can comprise a front sidewall 108A, an opposing rear sidewall 108B, and a pair of opposing sidewalls 108C that extend between respective edges of the front sidewall 108A and rear sidewall 108B. The intersections between the respective sidewalls can define rounded corners 110. Optionally, the sidewalls 108 can converge in a direction toward the floor 104 (i.e., slope inwardly moving in a downward direction) to provide draft angles for enabling manufacturing via injection molding. Optionally, the floor can comprise padding as is commonly used in conventional animal cages. The padding can be, for example, sawdust. Food pellets can be placed on the floor of the enclosure for foraging. A conventional water bottle can attach to the cage for hydrating the test subject. Optionally, the cage can comprise an opening within a sidewall of each enclosure to receive a dispensing portion of the conventional water bottle.

In exemplary aspects, and as shown in FIG. 3, the sidewalls 108 can define a plurality of apertures 130 for ventilation. One or more filters 132 can optionally cover the plurality of apertures in each sidewall 108. A frame 134 can extend about a perimeter of the filter 132 and receive fasteners (e.g., nuts 136 and bolts 138) to attach to the main body 102 of the cage assembly 100. In this way, the cage assembly is sealed so that all or substantially all ventilation to each enclosure travels through the at least one filter before entering a ventilation opening. Optionally, as shown in FIG. 3, a single filter 132 can cover a plurality of apertures 130 (optionally, all the apertures) of a sidewall 108. The filter can be removable, autoclavable, and replaceable. The filter can minimize penetration of infectious materials and bodies while enabling rapid air exchange. It is contemplated that a net, screen, grate, air-permeable membrane, or other permeable structure can be positioned between the plurality of apertures 130 in the cage and the filter 132 to inhibit the test subjects from chewing on the filter.

As shown in FIG. 3, a door 112 can pivotably couple to the main body portion 102 by a pair of hinges 114. In use, the door 112 can be moveable about and between (1) a closed position in which the door 112 cooperates with the sidewalls to provide the enclosure(s); and (2) an open position in which the door is pivoted away from the interior of the cage assembly to provide one or more openings through which the interior of the cage assembly can be accessed.

A cover 120 can extend across a top of the main body 102. The cover 120 can releasably attach to the main body 102 via latch 122. The latch 122 can pivotably attach to the main body 102 via hinges 124. A latch 126 that is pivotable about a hinge 128 can attach to the door 112. The latch 126 can releasably engage a catch on top of the cover 120 for holding the door 112 in a closed position. Optionally, the cover 120 can comprise one or more swivel housings 180 that are configured to receive at least a portion of a swivel as further disclosed herein.

A partition 140 can define a common sidewall that divides the interior of the cage into a first enclosure 142 and a second enclosure 144. The partition 140 can optionally be removable. The main body can optionally define a slot into which the partition 140 can be inserted. The partition 140 can define an opening 146 (optionally, a plurality of openings) between the first enclosure 142 and the second enclosure 144 for allowing respective test subjects 12 in each of the first and second enclosures to interact with each other (e.g., through vocal interaction, through scent, through body warmth, and the like). Thus, the first enclosure 142 and second enclosures 144 can each have respective sidewalls (or sidewall portions) defined by the front sidewall 108A, the door 112, the rear sidewall 108B, a sidewall 108C extending between the front and rear sidewalls, and the partition 140. In these examples, it is contemplated that the floor area within each enclosure can have a respective major dimension, which can be equal a maximum diagonal between corners of the enclosure.

The sidewalls (e.g., main body 104 and partition 140) and cover can optionally comprise polycarbonate and can optionally be autoclavable. Portions of the cage, such as, for example, the main body 102 and cover 120, can be transparent so that the test subject can be observed while closed in the cage.

Figure 6:
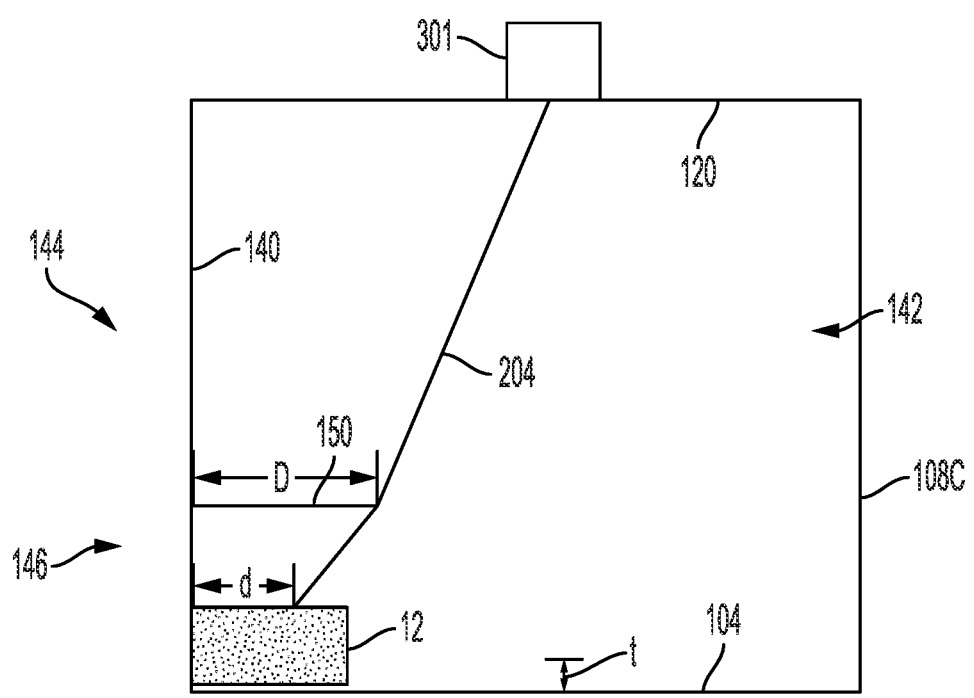
FIG. 6 is a schematic view of a test subject within an interior of the cage system of FIG. 3, approximating a cross section taken in the plane P of FIG. 5.
Figure 7:
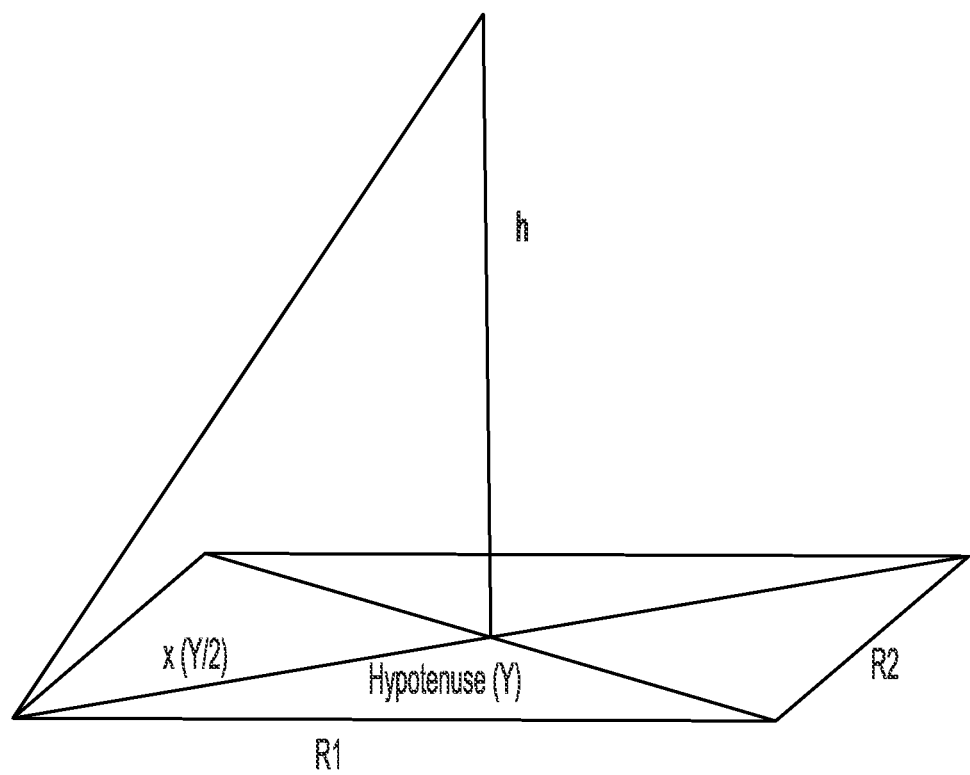
FIG. 7 is a schematic showing measurements of an interior of an enclosure of the cage system of FIG. 3.

Referring to FIG. 6, a shelter subassembly 150 can extend inwardly from the partition 140 into each of the first enclosure 142 and the second enclosure 144. Within each enclosure, the shelter subassembly 150 can comprise an arcuate roof, a pair of parallel walls extending vertically downward from the arcuate roof, and, optionally, a floor cover extending between bottom edges of the sidewalls of the shelter subassembly. Within each enclosure, the shelter subassembly 150 can project from the partition 140 a select distance D. Optionally, the distance D can be about 4-5 centimeters. It is contemplated that the distance D can be selected so that the cable will not restrict the test subject from interacting with the test subject of the opposing enclosure. For example, the cable can be strapped to the back of the test subject a select spacing, d, away from the subject's head. In this way, the test subject cannot chew on the cable. This select spacing can also enable the test subject to enter the shelter subassembly before the cable touches the shelter subassembly. Further, the cable can be sufficiently flexible to bend upon contact with the shelter subassembly. The select distance that the shelter subassembly 150 protrudes from the partition 140 can be selected so that the test subject (e.g., at least the nose and/or face of the test subject) can at least reach a plane defined by the partition 140 when the cable is fully taut against the shelter subassembly. As further disclosed herein, the cable length can be a function of the enclosure's dimensions. Thus, the select distance D that the shelter subassembly 150 protrudes from the partition 140 can be a function of the cable length and the enclosure's height and width dimensions.

The covers 120 for the first enclosure and the second enclosure can be unitarily constructed as a cover assembly 178. Optionally, the cover assembly 178 can comprise swivel housings 180. In these aspects, the cover assembly 178 can further comprise swivels 300, as further disclosed herein, with the swivels positioned within respective swivel housings 180. The cover assembly 178 can comprise first and second openings between the first and second enclosures and their respective swivels 300. The first and second openings can provide communication to enable the cable of the treatment assembly to couple to the respective swivel. Each swivel can be in overlying relation to a respective one of the first and second openings. According to various aspects, each swivel can extend through a respective opening in the cover assembly and at least partially into a respective enclosure to receive a respective cable. In further embodiments, each cable can extend through a respective one of the first and second opening to couple to the respective swivel.

Referring to FIGS. 4-7, the distance between the cover 120 and the floor 104 can define a cage height. In order to prevent the test subject from having sufficient slack in the cable 204 in order to flip over or get tangled with the cable, the cage assembly can have a select cage height, h, that is a function of the length, $R_1$, and width, $R_2$, of each enclosure. For example, cable 204 can have a select length to prevent providing enough slack for the test subject to wrap the cable around its body. According to some optional aspects, the dimensions of each enclosure 142,144 can be selected so that the test subject can access the corners of the cage, but when the test subject is positioned directly below the attachment of the cable to the swivel 300, the cable does not have enough slack to hang or extend downwardly from the back of the test subject and touch the floor of the cage. To maximize the usable area for a given cage height, the cable can extend from directly above a center of the floor space of each enclosure. Accordingly, the height of the cage can be selected as a function of the major dimension of the cage floor (of a given enclosure) and the height of the test subject. For example, the height can be selected based on the following equation:

$$h \geq (R_1^2 + R_2^2 - 16a^2)/16a$$

where h is the height of the cage, $R_1$ is a length of the enclosure, $R_2$ is width of the enclosure, and a is the height of the animal.

Thus, the height can be a function of the major dimension of the cage floor, Y, according to the following equation:

$$h \geq (Y^2 - 16a^2)/16a$$

A typical test subject mouse can have a height (a) of 20 mm. Thus, in some examples, the cage height, h, in millimeters, can be a function of the major dimension of the cage floor, Y (in millimeters), according to the following equation:

$$h \geq (Y^2 - 6400)/320 \text{ [mm]}.$$

More generally, the height of the cage can be selected as the major dimension of the cage floor (of a respective enclosure) multiplied by a factor. According to some aspects, the cage can have a height of at least 0.5 times the major dimension of the cage floor, at least 0.6 times the major dimension of the cage floor, at least 0.7 times the major dimension of the cage floor, at least 0.8 times the major dimension of the cage floor, or at least the major dimension of the cage floor, or at least 1.1 times the major dimension of the cage floor, or at least 1.2 times the major dimension of the cage floor.

In some exemplary embodiments, the floor of the cage assembly can have a length of about 315 mm and a width of about 185 mm. Thus, with a partition dividing the length of the floor, each enclosure can have a floor with a long side of 185 mm and a short side of 157 mm. Thus, the floor area of each enclosure can have a major dimension of 242 cm (equal to the maximum diagonal between corners of the enclosure).

Thus, it is contemplated that the height of the cage can have a minimum height of at least 163 mm, providing a height that is about 0.7 times the major dimension of the cage floor. According to various aspects, the floor area of each enclosure can have a minimum major dimension of at least 160 mm, between about 160 mm and about 200 millimeters, between about 200 millimeters and about 250 mm, between about 250 mm and about 300 mm, between about 300 mm and about 400 mm, or above 400 mm. In some embodiments, the cage height can be about 260 mm. In further embodiments, the height of the cage can be at least 60 mm, at least 105 mm, at least 175 mm, at least 261 mm, or at least 480 mm.

It is contemplated that the above equations for selecting the height of the cage are not absolute because the cable has some amount of rigidity (i.e., the cable has a limit to its flexibility), thereby limiting the ability of the cable to reach the floor of the cage. Thus, it is contemplated that the height of the cage can be less than the minimum heights of the above equations while still providing a sufficient cage height to prevent entanglement of the test subject.

Optionally, the cage can comprise a feeder (e.g., a food tray or food dispenser). The feeder can optionally couple to the partition 140 or other sidewall so that the feeder remains suspended.

The Treatment Assembly

Referring to FIG. 8, the treatment assembly 200 can be configured for providing TTFields to an organ tumor. The treatment assembly 200 can comprise a flexible circuit board 202 that includes a connector end 206, and one or more lead ends 208 at the ends of respective electrical leads 205 opposite the connector end 206. The electrical leads 205 can be provided as components of a cable 204. Optionally, the flexible circuit board 202 can be configured to couple to a swivel 300. The cable 204 can be elongate and sufficiently flexible to allow an amount of twisting without requiring a swivel. The connector end 206 can optionally be a USB-C connector (e.g., a male USB-C connector). It is contemplated that the use of a flexible circuit board 202 as disclosed herein can provide a plurality of electrical leads 205 as part of a unified structure, thereby avoiding tangled cables or wires and minimizing the space occupied by the electrical leads. Thus, in some aspects, the cable 204 can be defined by a portion of the flexible circuit board 202.

In a pre-use configuration, as shown in FIG. 8, the lead ends 208 can be spaced along a longitudinal dimension 201 of the treatment assembly 200. Optionally, the lead ends 208 can be arranged in one or more longitudinally extending rows. For example, the lead ends 208 can be arranged in two rows of four lead ends, wherein the two rows extend in the longitudinal dimension 201. As another example, the one or more longitudinally extending rows can comprise a single row of lead ends 208. However, it is contemplated that any desired arrangement of lead ends can be used. The cable 204 can extend perpendicularly, or substantially perpendicularly relative to the longitudinal dimension 201.

Each lead end 208 can be configured to engage or couple to a respective plate 210. Thus, the treatment assembly 200 can comprise a plurality of electrodes, with each electrode comprising a lead end 208 that is in contact with or otherwise coupled to a respective plate 210. In some optional embodiments, at least one (optionally, each) plate 210 can be a ceramic plate. In other embodiments, such as those in which the treatment assembly 200 functions as a control heating device, it is contemplated that at least one (optionally, each) plate can be a glass plate. In still further aspects, other types of electrodes are contemplated, such as, for example, electrodes formed from metal or other electrically conductive materials.

The treatment assembly 200 can comprise an inner layer 212 having an outer surface 214 and an inner surface 216. The inner layer 212 can comprise a biocompatible, breathable adhesive, such as, for example, polyurethane. In some embodiments, the inner layer can comprise VANCIVE MED 9598A polyurethane film with acrylic adhesive. The inner layer 212 can define a plurality of openings 218 therethrough for receiving respective plates 210. The openings 218 can be longitudinally spaced along the inner layer. Although depicted as receiving individual plates, it is contemplated that each opening can optionally receive a plurality of plates (e.g., two plates) therein.

The plates 210 can have upper surfaces 220 and lower surfaces 222. The upper surfaces can be disposed against the electrical leads 208. A layer of hydrogel 224 can be disposed against the lower surfaces 222 of each of the plates 210. The layer of hydrogel 224 can optionally cover at least two adjacent plates 210. Optionally, the layer of hydrogel 224 can cover the lower surfaces 222 of the plates 210 and adjoining portions of the inner surface of the inner layer 212. The layer of hydrogel 224 can be, in some optional aspects, about 0.6 mm thick. The hydrogel 224 can comprise, for example, AG625 sensing gel made by AXELGAARD.

A cover layer 230 can attach to the outer surface 214 of the inner layer 212. The cover layer 230 can overlie the plurality of electrical leads 208 of the flexible circuit board 202. The cover layer 230 can comprise one or more tab portions that extend beyond a perimeter of the inner layer 212. For example, the cover layer 230 can comprise two opposing tab portions 232 that are complementary to one another when the cover layer defines a circumferential loop (e.g., when wrapped around a torso of a test subject, as further disclosed herein). Optionally, the tab portions 232 can be about half of the width of the cover layer where they intersect a main body portion of the cover layer. When the cover layer is wrapped around the torso of the test subject, the tab portions 232 can extend past each other to attach to respective portions of the cover layer on ends of the cover layer opposite the respective tab portions.

According to some optional aspects, the cover layer can have an inner surface that comprises a biocompatible non-woven adhesive. The non-woven adhesive can optionally be elastic in the longitudinal dimension 201. In some embodiments, the cover layer can comprise Product No. 1776 medical nonwoven tape made by 3M.

A release layer 250 can contact and cover the underside of the biocompatible breathable polyurethane adhesive on the inner surface 216 of the inner layer 212 as well as the underside of the hydrogel layer 224. The release layer can protect the adhesive prior to attaching the treatment assembly to the test subject. The release layer 250 can have a shape that is complementary to the shape of the cover layer 230. The release layer can comprise separate tabs 252 that are configured to cover the tab portions 232 of the cover layer 230.

Figure 10A:
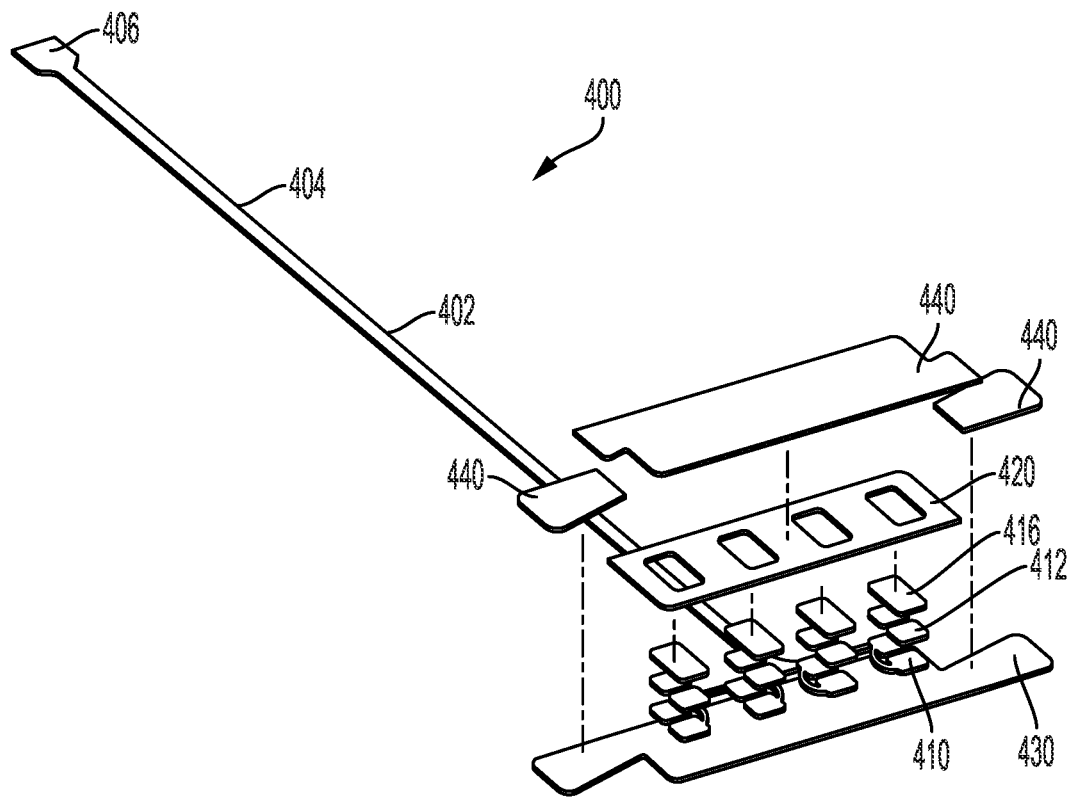
FIG. 10A is an exploded view of a control heater assembly in accordance with embodiments disclosed herein.
Figure 10B:
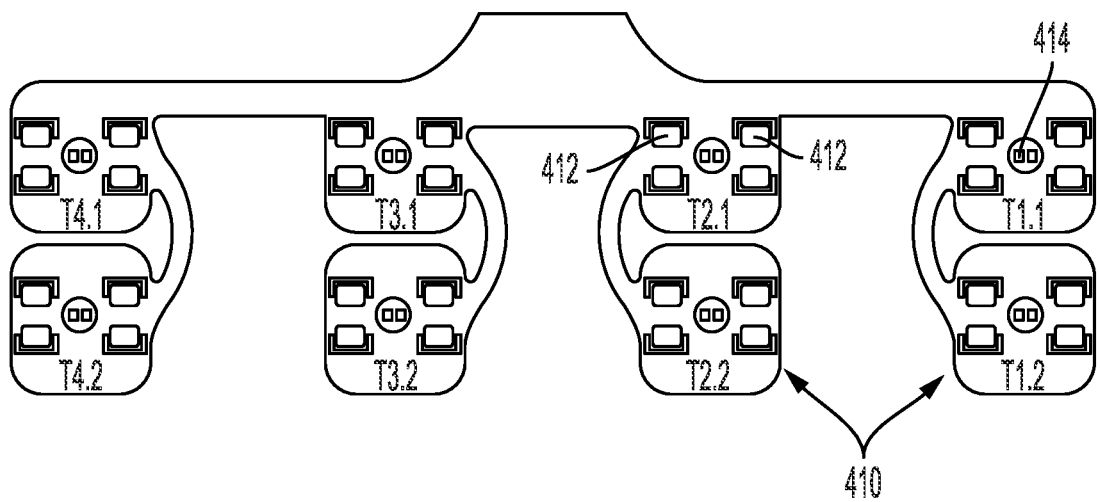
FIG. 10B is a portion of a circuit board of the control heater assembly of FIG. 10A.
Figure 11A:
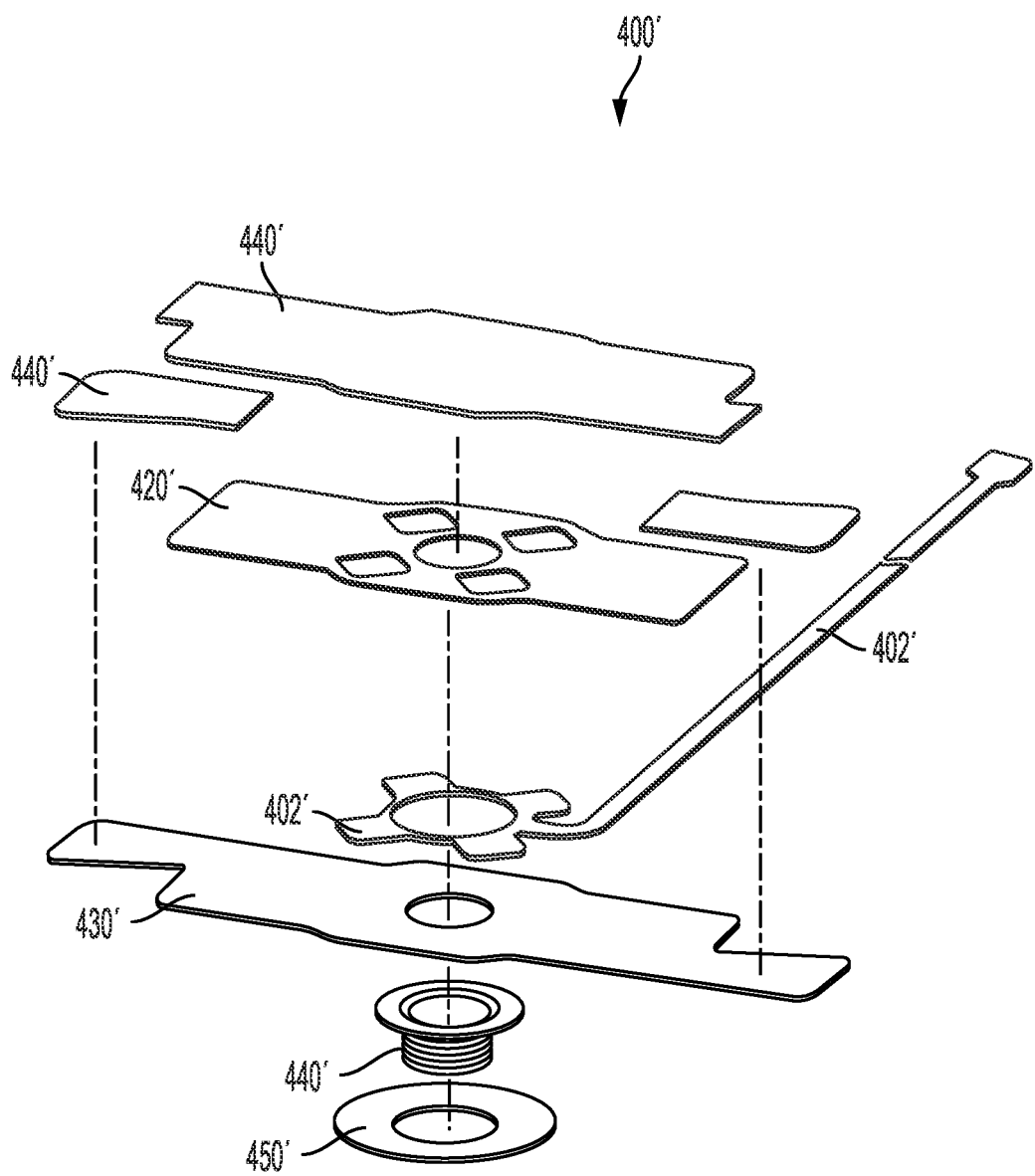
FIG. 11A is an exploded view of another control heater assembly in accordance with embodiments disclosed herein.
Figure 11B:
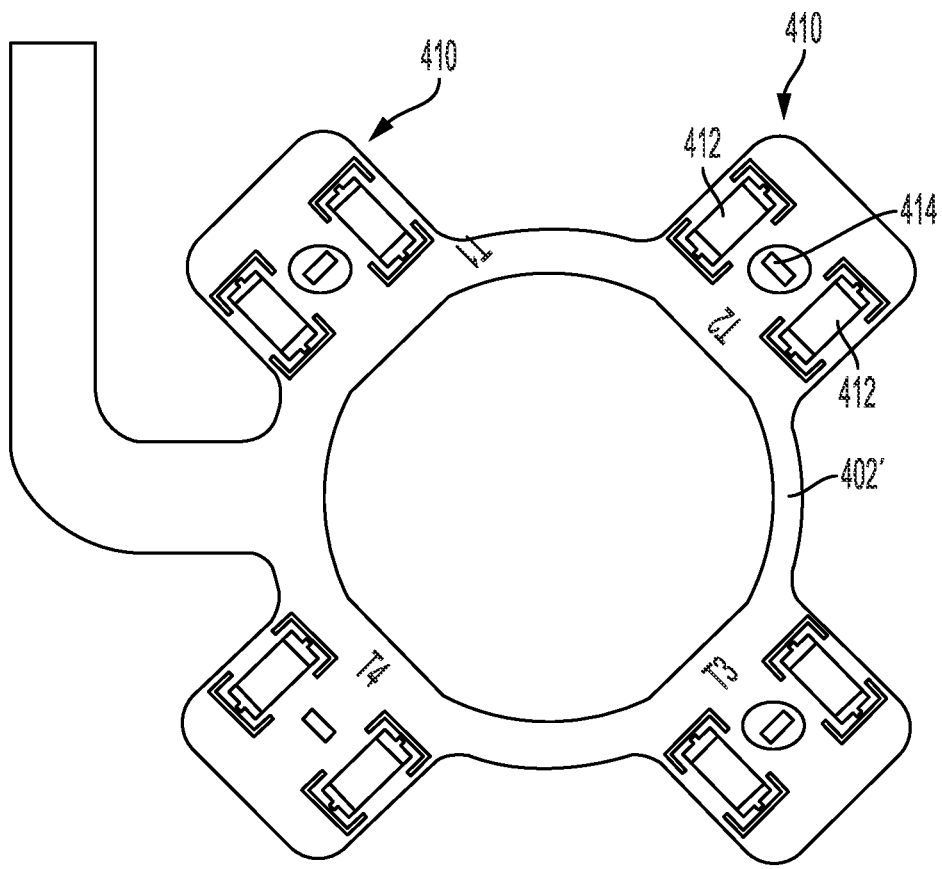
FIG. 11B is a portion of the circuit board of the control heater assembly of FIG. 11A.

The treatment assembly can comprise at least one temperature sensor 260 (not shown, but the temperature sensors 260 can have corresponding positions to the temperature sensors 414 and 414' of FIGS. 10B and 11B), such as, for example, thermistors or thermocouples. The at least one temperature sensor can optionally be integral to the flexible circuit board 202. The at least one temperature sensor can comprise a plurality of temperature sensors. For example, a temperature sensor can be positioned on the flexible circuit board 202 proximate to each lead end 208. The temperature sensor(s) 260 can provide feedback to prevent overheating of the treatment assembly or causing burns to the test subject. For example, based on temperature readings from the temperature sensors 260 exceeding a threshold (e.g., 40° C.), the TTField generator 18 can adjust or stop induction of TTFields at one or more electrodes. Additionally the system 10 can receive feedback from the temperature sensors 260 in order to maintain a consistent temperature in control heater treatment assemblies that are disclosed further herein. Optionally, the temperature sensors can be positioned within respective holes in the respective plates to measure the temperature between the plates and the hydrogel. In further aspects, the temperature sensors can be positioned on sides of the respective plates opposite the hydrogel, thereby avoiding the need for forming holes in the plates (and potentially making the plates undesirably fragile). In further embodiments, the temperature sensors can be positioned at portions of the hydrogel to the side of the respective plates (e.g., within three millimeters of the plate edge). For example, as shown in FIG. 10A, pairs of plates 412 can share a single layer of hydrogel 410, and each temperature sensor can be positioned between a respective pair of plates.

The portion of the treatment assembly bearing against the test subject (e.g., excluding the weight of the cable) can optionally weigh less than about ten percent of the body weight of the subject. For example, the portion of the treatment assembly bearing against the test subject can weigh less than about 2.5 grams for a typical mouse.

The treatment assembly can be sufficiently flexible to conform to a portion of a torso of the test subject 12. Optionally, in a pre-use configuration as shown in FIG. 8, the treatment assembly has a length in the longitudinal dimension 201 that is sufficient to extend around a girth of the torso of the test subject (when positioned on the animal and during use). Optionally, the treatment assembly can be pre-formed into a three dimensional shape that is configured to be complementary to the shape of the torso of the test subject 12.

Optionally, a kit can comprise a plurality of treatment assemblies 200 having varying lengths in the longitudinal dimension 201 (in pre-use configurations). In this way, a test subject can be fitted with a properly sized treatment assembly (depending upon the girth/circumference of the animal). For example, the properly sized treatment assembly can snugly wrap around the girth of the torso of the test subject. Optionally, an additional cover material (that can be, for example, the same material as the outer layer) can be provided for reinforcing attachment to the test subject and sealing edges of the adhesive materials from dirt and debris that could inhibit good contact.

Figure 9:
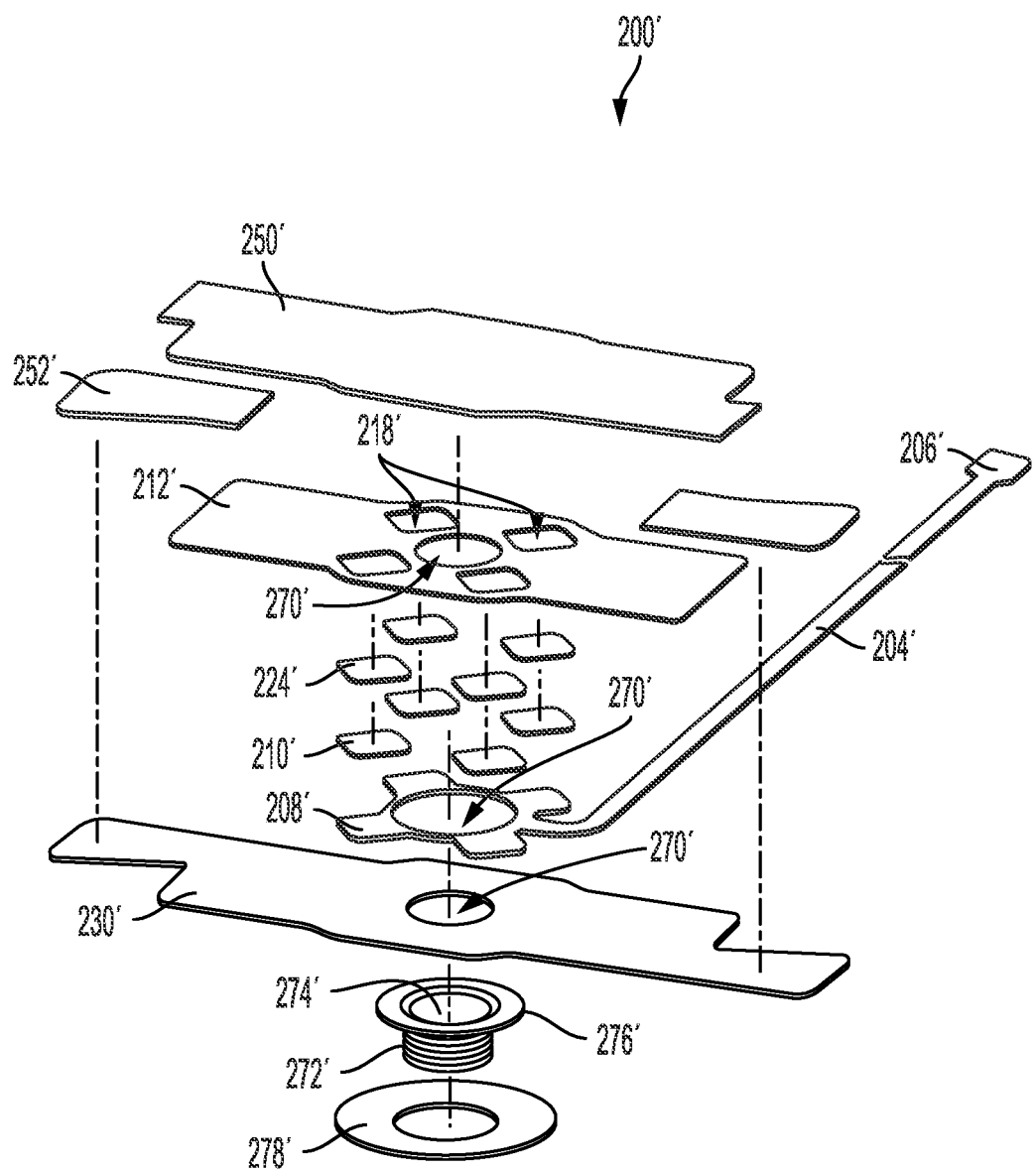
FIG. 9 is an exploded view of another treatment assembly, in accordance with embodiments disclosed herein, for use with the system as in FIG. 1.

Referring to FIG. 9, a treatment assembly 200' can be configured for treating a subcutaneous tumor. The treatment assembly 200' can have a generally similar construction as that of the treatment assembly 200, having an inner layer 212' defining openings 218' that receive plates 210' therein. Optionally, it is contemplated that hydrogel 224' can be received within openings 218'. A flexible circuit board 202' can comprise a cable 204', a connector end 206' that is configured to couple to a swivel 300 (FIG. 1), and one or more lead ends 208' at the lead ends opposite the connector end 206'. The lead ends 208' can be configured to couple to respective plates 210'. An outer layer 230' can be attached to respective upper surfaces of the inner layer and the lead ends. A release layer 250', comprising separate tabs 252', can attach to an underside of the inner layer 212' and hydrogel 224'. The outer layer 230' and release layer 250' can be similarly constructed to that of the outer layer 230 and release layer 250.

The inner layer 212', circuit board 202', and cover layer 230' can cooperate to define a through-hole 270' that extends through the thickness of the treatment assembly 200' (other than an inner release layer, when present) and is configured to receive a subcutaneous tumor. Optionally, the through-hole 270' can have a diameter of between ten and fifteen mm. Optionally, the through-hole 270' can have a maximum diameter of about fifteen mm. A cap 272', defining a receptacle 274' therein that is configured to receive an outwardly extending portion of a subcutaneous tumor, can extend across the through-hole 270'. The cap 272' can be attached to the cover layer 230. For example, the cap 272' can define a radially extending peripheral rim 276'. An adhesive ring 278' can engage the flange 276' and outer layer 230' to secure the cap 272' to the outer layer. The cap 272' can inhibit dirt and debris (e.g., sawdust floor cover) from entering the hole and inhibiting contact between the treatment assembly and the test subject.

In exemplary aspects, the openings 218' within which plates 210' are received can have a predetermined relationship relative to through-hole 270'. Optionally, in these aspects, and as shown in FIGS. 9 and 11A, the openings 218' can be circumferentially spaced about a perimeter of the through hole 270' (and, thus, the subcutaneous tumor, when the tumor extends through the through-hole 270').

According to some aspects, a kit can comprise a plurality of treatment assemblies 200' having through-holes 270' of varying diameters and correspondingly varyingly sized caps 272'. The plurality of treatment assemblies 200' having through-holes of varying diameters can optionally have correspondingly varying spacing between lead ends 208' and plates 210'. In this way, the test subject 12 can be fitted with a treatment assembly 200' that is suitably sized for its subcutaneous tumor. Optionally, the kit can further comprise a plurality of caps (optionally, same-sized and/or of varying sizes) so that the caps can be replaced over the course of the treatment.

The length of the cables 204,204' can be selected based on the enclosure dimensions so that the test subject 12 cannot get wrapped up by or entangled with the cable. Some amount of slack can be attached to the test subject's back in order to reduce the amount of free length of the cable. Thus, the cable can have an operative portion that is not attached to the test subject, wherein the operative portion can define an operative length of the cable. According to some aspects, the operative length of the cable can be selected so that the cable does not have sufficient length to hang from the test subject's back and touch the floor when the test subject is directly below the swivel. Thus, it can be understood that a maximum operative length of the cable can be approximated as the height of the cage (or the height at which the cable attaches to the swivel) plus two times the height of the test subject. In further aspects, the cable length can be selected so that the cable does not have enough slack to hang from the back of the test subject to within a threshold distance, t, (FIG. 6) of the floor of the cage. Thus, a maximum operative length of the cable can be approximated as the height from the floor at which the cable attaches to the swivel plus two times the height of the test subject, minus two times the threshold distance. Optionally, the threshold distance can be zero millimeters, one millimeter, two millimeters, four millimeters, six millimeters, ten millimeters, or more. In some aspects, the threshold distance can range from about 1 mm to about 10 mm or from about 2 mm to about 6 mm. It is still further contemplated that because of the limited flexibility of the cable, the length of the operative portion of the cable can be slightly greater than two times the height of the subject plus the height of the cage without the cable being able to reach the floor of the cage.

To construct a treatment assembly 200, each plate of a plurality of plates 210 can be positioned within openings in the inner layer of the treatment assembly. For example, in some embodiments, a pair of plates can be positioned within each opening. Alternatively, a single plate can be positioned within each opening. Each lead end of the plurality of lead ends can be positioned in contact with a respective plate of the plurality of plates. As stated previously, lead ends, when coupled with plates as disclosed herein, form respective electrodes. The cover layer can be attached to the outer surface of the inner layer so that the cover layer overlies the plurality of electrodes. A layer of hydrogel can be applied to lower surfaces of each plate of the plurality of plates. In some aspects, a pair of plates positioned within a shared opening in the inner layer can also share a layer of hydrogel. Optionally, hydrogel can be applied over adjoining portions of the inner surface of the inner layer.

Figure 26:
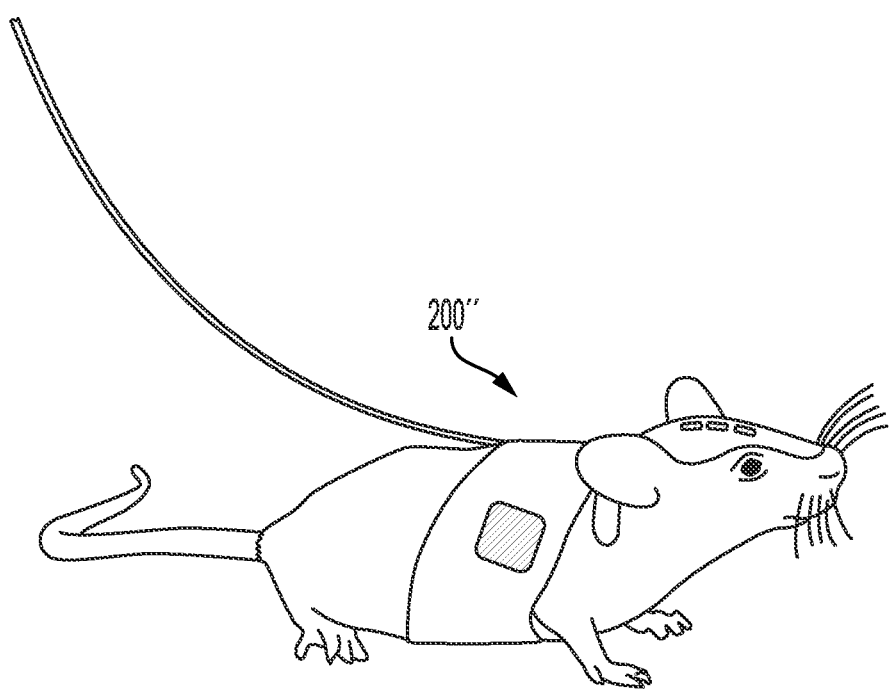
FIG. 26 is a perspective view of the treatment assembly of FIG. 24 positioned on a test subject.
Figure 27:
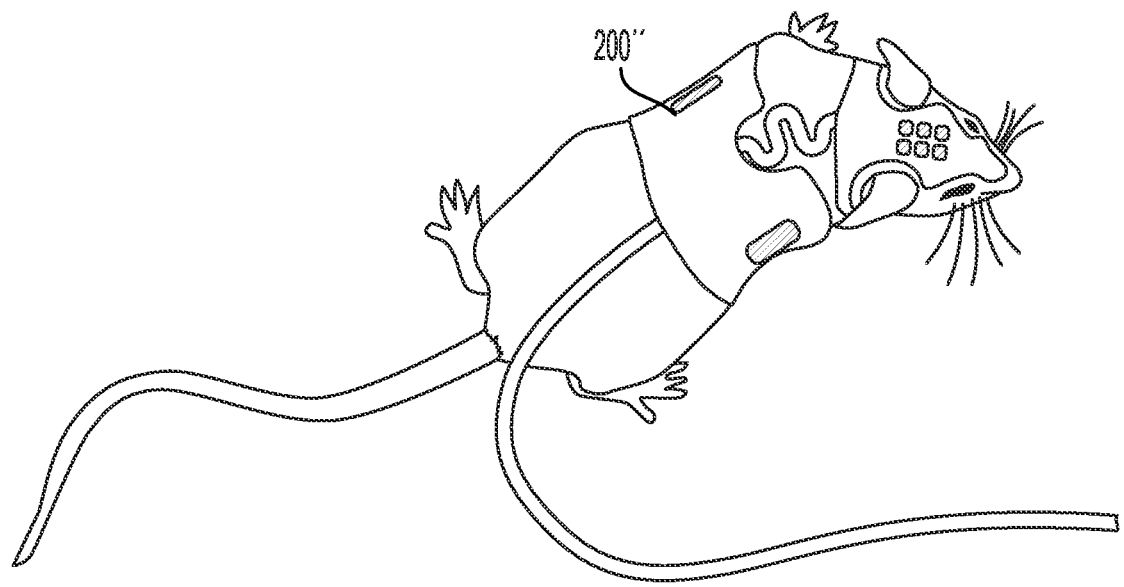
FIG. 27 is a top view of the treatment assembly of FIG. 24 positioned on the test subject.

Referring to FIGS. 24-29, in further aspects, it is contemplated that a treatment assembly 200" can be configured to be positioned at least partly on the head of the test subject. For example, a head-covering portion 9a of the treatment assembly 200" can be coupled to at least a portion of the head of a mouse as shown in FIG. 26. The head-covering portion 9a of the treatment assembly 200" can comprise a head-wearable layer 6 that is configured to extend over a portion of the head of the test subject and be coupled to the test subject through an adhesive that is positioned on one or more inner surfaces of the head-wearable layer 6. The treatment assembly 200" can further comprise a torso-covering portion 9b that is configured to be positioned on the body (e.g., torso) of the test subject (e.g., wrapped around the body/torso of the test subject, as further disclosed herein). The torso-covering portion 9b of the treatment assembly 200" can comprise an inner adhesive wearable layer 1 that is configured to engage the body (optionally, the skin) of the test subject. A flexible circuit board 5 can comprise a plurality of lead ends. An end 8 of the flexible circuit board can be in communication with the TTFields generator 18 (FIG. 1). An inner adhesive patch 4 can be coupled to a skin engagement side of the adhesive portion 6 with a portion of the flexible circuit board 5 positioned therebetween. An outer wearable layer 7 can be coupled at an outer side of the torso-covering portion 9b of the treatment assembly.

Plates (e.g., ceramic plates) 3 can be coupled to the lead ends of the flexible circuit board. Hydrogel 2 can be positioned below the ceramic plates to engage the skin of the patient. The inner adhesive wearable layer 1 of the torso-covering portion 9b can define at least one opening (optionally, a plurality of openings) that receives a corresponding portion of hydrogel 2.

Figure 28:
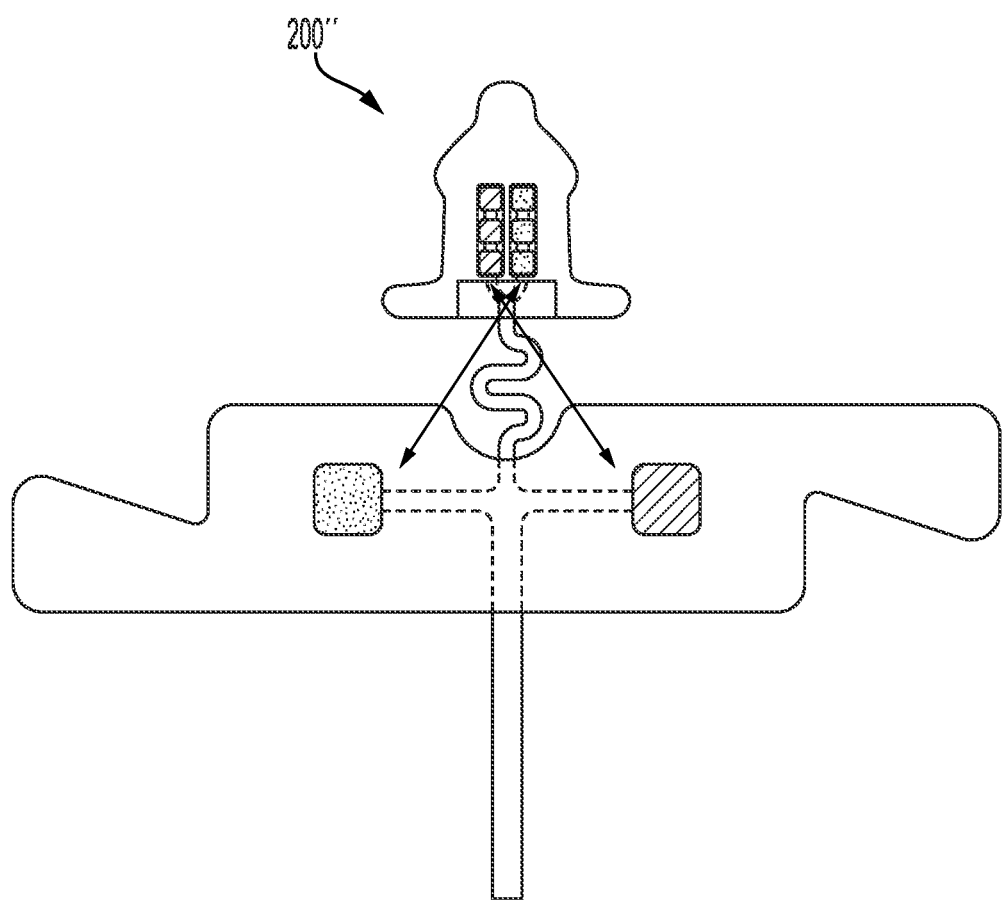
FIG. 28 is a top view of the treatment assembly of FIG. 24, showing communication between electrodes.

The flexible circuit board 5 can comprise a plurality of lead ends (and, accordingly a plurality of electrodes 602) that are configured to be positioned on the head of the test subject and one or more lead ends (e.g., two lead ends) (and, accordingly a plurality of electrodes 604) that are configured to be positioned on the body (e.g., torso) of the test subject. In exemplary aspects, the plurality of lead ends (for positioning on the head) are configured to underlie the head-wearable layer 6, and the one or more lead ends (for positioning on the torso) are configured to underlie the outer wearable layer 7 of the torso-covering portion 9b, with each lead end overlying a respective ceramic plate 3 and hydrogel portion 2. Optionally, the plurality of lead ends that are configured to be positioned on the head of the test subject can comprise a first group of lead ends (e.g., three lead ends, corresponding to electrodes 602a) that are configured to be positioned on a first side (relative to a median plane 606 that bisects the test subject into left and right sides) of the head of the test subject and a second group of lead ends (e.g., three lead ends, corresponding to electrodes 602b) that are configured to be positioned on a second opposing side (relative to the median plane) of head of the test subject. The one or more lead ends that are configured to be positioned on the body (e.g., torso) of the test subject can comprise a first lead end (corresponding to electrode 604a) that is positioned on the first side of the body of the test subject relative to the median plane and a second lead end (corresponding to electrode 604b) that is positioned on the second side of the body of the test subject relative to the median plane. Referring to FIG. 28, it is contemplated that the first lead end that is positioned on the first side of the body can cooperate with the second group of lead ends on the second side of the head of the test subject to provide TTFields, and the second lead end that is positioned on the second side of the body (torso) can cooperate with the first group of lead ends on the first side of the head of the test subject to provide TTFields. The TTFields can be provided in an alternating fashion to provide or promote crossing of TTFields.

In exemplary aspects, the flexible circuit board 5 can comprise an undulating (e.g., switchback), serpentine, wave-like, or zig-zag portion (generally referred to as an "alternating-profile portion" 700) that is configured to promote flexibility to allow the test subject to move its neck. In use, it is contemplated that the alternating profile of this portion of the flexible circuit board 5 can provide a reduced starting length (to avoid unnecessary slack in the cable) while also permitting straightening to increase the length and accommodate movement (e.g., neck extension, twisting, and turning) of the test subject. In these aspects, and as shown in FIGS. 24-25 and 27-29, the alternating-profile portion can be positioned between the head-covering portion 9a and the torso-covering portion 9b. It is further contemplated that the alternating-profile portion of the flexible circuit board 5 can be positioned between the plurality of lead ends (for positioning on the head) and the at least one lead end (for positioning on the torso).

Figure 29:
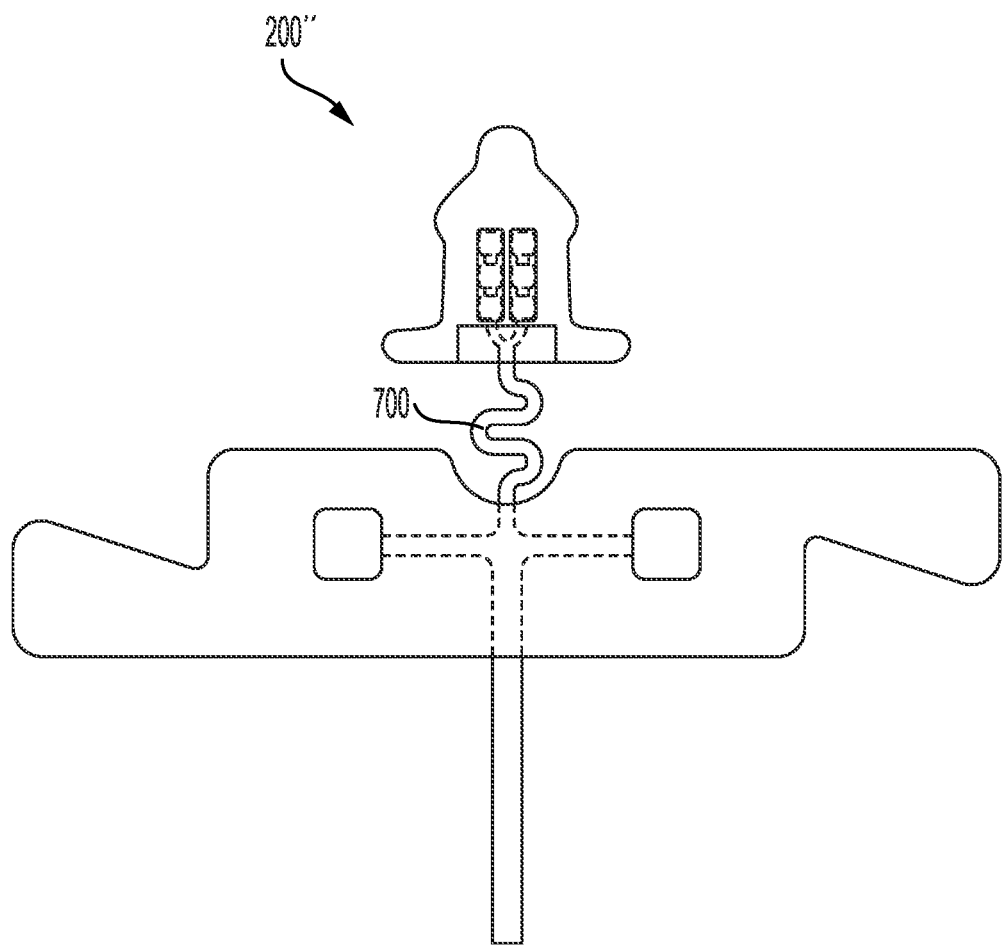
FIG. 29 is a top view of the treatment assembly of FIG. 24, showing an alternating-profile portion.

Exemplary, non-limiting dimensions of the treatment assembly 200" are provided in millimeters within FIG. 29.

It is contemplated that the materials and properties of the inner adhesive wearable layer 1 of the torso-covering portion 9b can be the same or similar to those of the cover layers 212, 212' disclosed herein with respect to treatment assemblies 200, 200'. Similarly, it is contemplated that the materials and properties of the hydrogel 2 of the treatment assembly 200" can be the same or similar to those of the hydrogel 224, 224' disclosed herein with respect to treatment assemblies 200, 200'. It is further contemplated that the materials and properties of the plates 3 of the treatment assembly 200" can be the same or similar to those of the plates 210, 210' disclosed herein with respect to treatment assemblies 200, 200'. It is further contemplated that the materials and properties of the flexible circuit board 5 can be the same or similar to those of the flexible circuit board 202, 202' disclosed herein with respect to treatment assemblies 200, 200'. It is still further contemplated that the materials and properties of the head-wearable layer 6 and the outer wearable layer 7 of the treatment assembly 200" can be the same or similar to those of cover/outer layers 230, 230' disclosed herein with respect to treatment assemblies 200, 200'.

Referring to FIGS. 10A-11B, a control heater treatment assembly 400 can be coupled to a control test subject and can be configured to mimic many or all or substantially all of the aspects of the treatment assembly 200. Likewise, a control heater treatment assembly 400' can be configured to mimic or all or substantially all of the aspects of the treatment assembly 200' and can have a similar construction and operation to that as described for the control heater treatment assembly 400. Similarly, a control heater treatment assembly can be configured to mimic all or substantially all of the aspects of the treatment assembly 200'' and can have a similar construction and operation to that as described for control heater treatment assembly 400. For example, the control heater treatment assembly 400 can be configured to generate heat to maintain a similar temperature against the control test subject's skin, thereby limiting differences between aspects of the control group and the test group. As another example, the control heater treatment assembly 400 can be configured to have substantially or generally the same weight as the treatment assemblies that are capable of generating TTFields as further disclosed herein.

The control heater assembly 400 can comprise a flexible circuit board 402. The flexible circuit board 402 can include a cable 404 and a connector end 406 that is configured to couple to a swivel 300. The flexible circuit board can comprise a plurality of resistive heaters positioned in locations corresponding to where the electrodes are positioned in a treatment assembly 200. For example, the flexible circuit board 402 can comprise eight zones 410 (e.g., two rows of four zones 410) where the electrodes would be in a corresponding treatment assembly. More generally, the flexible circuit board 402 can have any desired number of zones, each zone corresponding to a location of an electrode in a corresponding treatment assembly. Optionally, each zone 410 can comprise two resistive heaters 412 (shown schematically in FIG. 10A as a single unit that is disassociated from the circuit board 402 and in FIG. 11 in detail as components of the circuit board 402). A temperature sensor 414 can be disposed in each zone 410, optionally, in a center of each zone 410 equally spaced between the heaters 412. The heaters 412 can optionally comprise glass plates.

Optionally, the control heater assembly 400 can comprise an inner layer 420 that defines a plurality of through-holes through which the heaters 412 can be positioned. Optionally, the control heater assembly 400 can comprise a cover layer 430 that extends across the upper side of the flexible circuit board. A release liner 440 can releasably attach a lower surface of the inner layer. The inner layer 420 and cover layer 430 can comprise the same materials and the same geometry of the corresponding treatment assembly in order to feel similar to the test subject. Optionally, a layer of hydrogel 416 can cover the lower sides of the flexible circuit board 402. Likewise, a control heater assembly 400' can have a corresponding structure to that of the treatment assembly 200', having a flexible circuit board 402', an inner layer 420', a release liner 440', a cover liner 430', a cap 450', and an adhesive ring 460'. Similarly, a control heater assembly that simulates the shape, weight, heat, and otherwise perceived experience of the treatment assembly 200'' is further contemplated.

The control heater assembly 400 can couple to the TTFields generator 18 via the swivel 300. The swivel 300 can control the output of the resistive heaters 412 based on feedback from the temperature sensors 260. In some embodiments, the control heater assembly 400 can maintain a set temperature (e.g., 38.5 or 39 degrees Celsius) to mimic the temperature that the corresponding treatment assemblies 200,200', 200'' reach as a byproduct of providing TTFields. In further embodiments, control heater assembly 400 can be selectively controlled to maintain a temperature that matches the temperature of treatment assemblies on corresponding test subjects receiving TTFields treatment.

The control heater assembly 400, 400' can further have a weight that is similar to that of the respective treatment assembly 200, 200', 200''. Thus, the control heater assembly can create the same perceived experience in the test subject. In this way, effects of the TTFields on the tumor development can be isolated from other aspects of the testing procedure.

In exemplary aspects, kits having both control heater assemblies 400, 400' and treatment assemblies 200, 200', 200'' can be provided. In these aspects, it is contemplated that each treatment assembly provided in the kit can have a corresponding/counterpart control heater assembly positioned within the same kit, thereby maximizing uniformity among control and experimental/treatment groups.

It is contemplated that embodiments disclosed herein can, in addition to providing TTFields, be used to provide other electric currents, fields, and heat to different body parts of test subjects.

In some optional aspects, a wide treatment assembly (and corresponding control heater assembly) for a test subject with a wide torso can have a length of about 200 mm to about 250 mm (relative to the longitudinal axis 201), a width of about 100 mm to about 130 mm (optionally, 110 mm to 115 mm), and a thickness of about 1.6 mm to about 1.7 mm. In some optional aspects, a narrow treatment assembly (and corresponding control heater assembly) for a test subject with a narrow torso can have a length of about 200 mm to about 250 mm, a width of about 80 mm to about 115 mm (optionally, 100 mm to 110 mm), and a thickness of about 1.6 mm to about 1.7 mm. In further optional aspects, a treatment assembly for a subcutaneous tumor (and corresponding control heater assembly) can have a length of about 290 mm to about 330 mm, a width of about 65 mm to about 95 mm, and a thickness of about 1.6 mm to about 1.7 mm.

Collar

Figure 30:
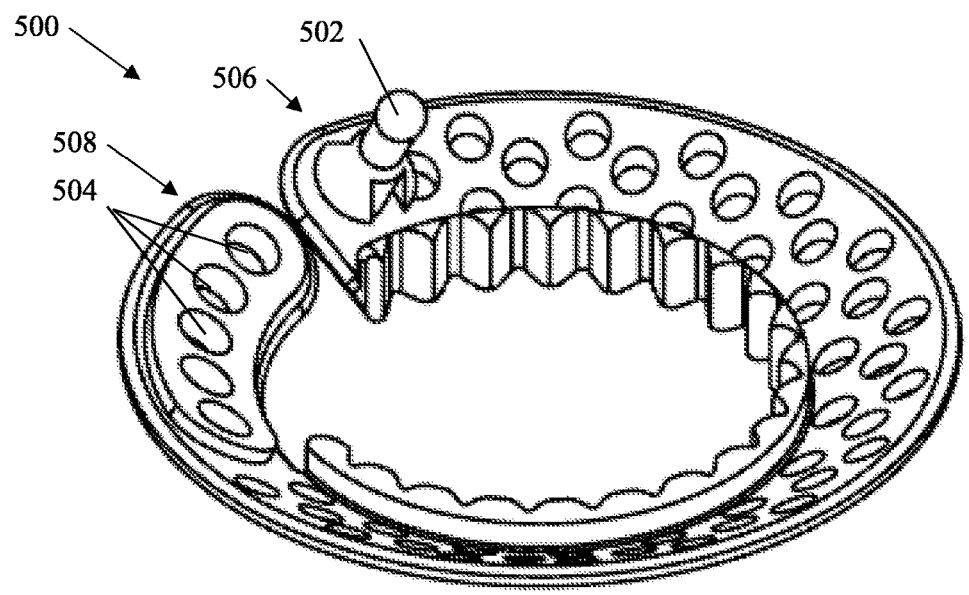
FIG. 30 is a side view of a collar in accordance with embodiments disclosed herein.
Figure 31:
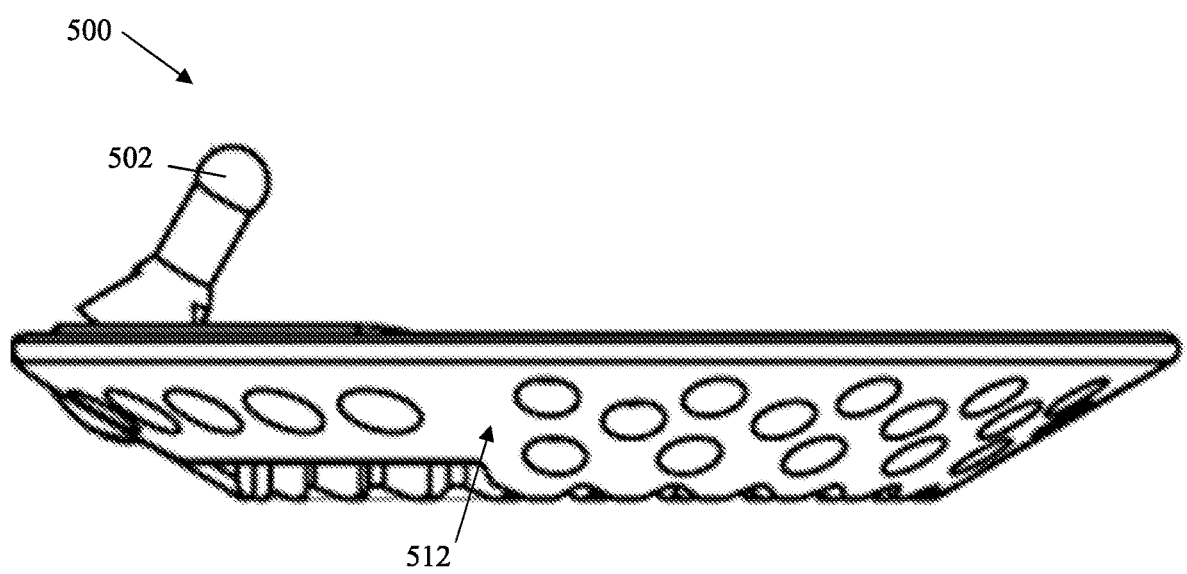
FIG. 31 is a side view of the collar of FIG. 30.
Figure 32:
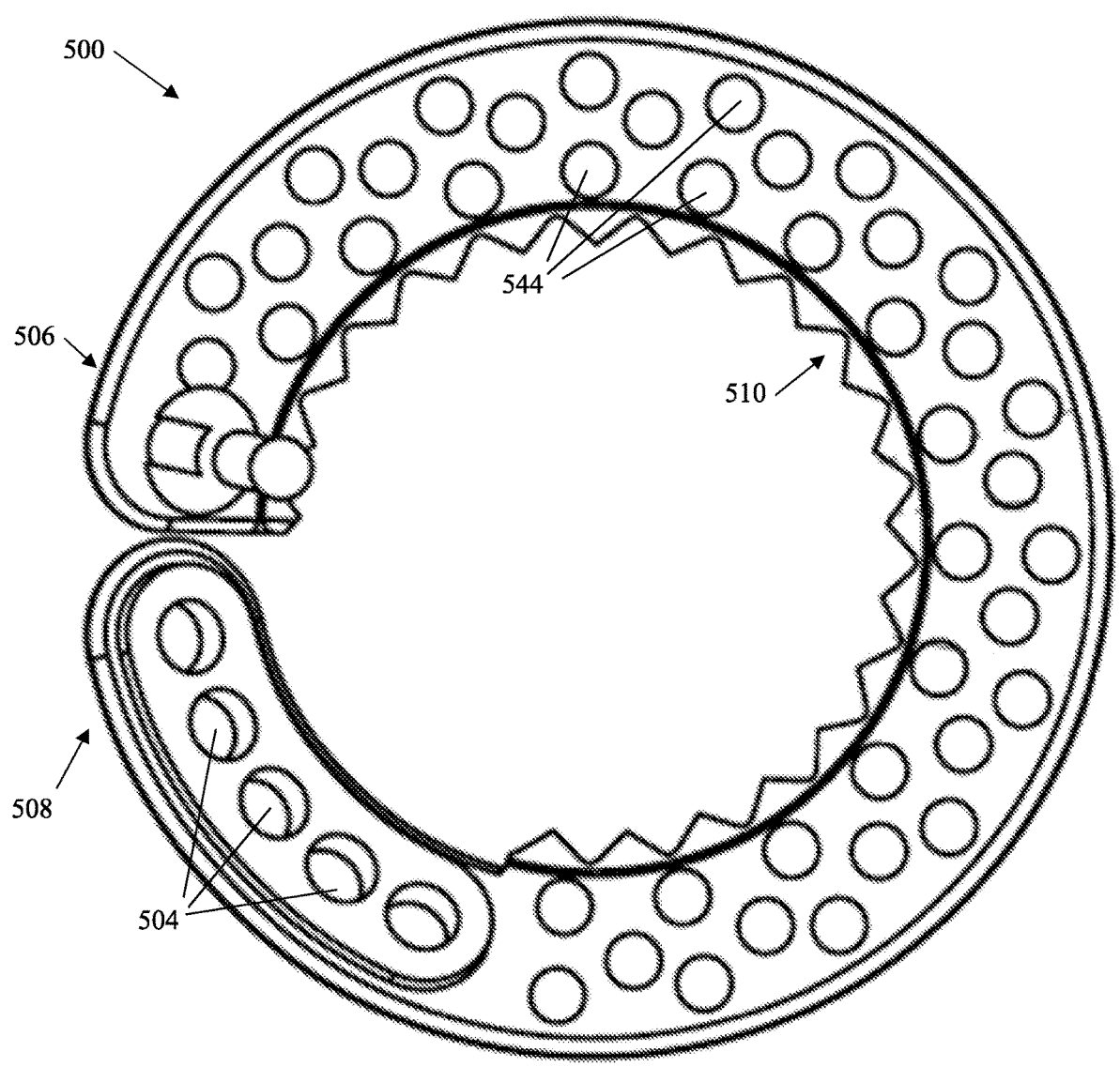
FIG. 32 is a top view of the collar of FIG. 30.

It is contemplated that the test subjects can be prone to chew or gnaw on the treatment assemblies 200, 200', 200'' or the control heater treatment assemblies 400, 400'. Referring to FIGS. 30-32, in order to inhibit such behavior, it is contemplated that a collar 500 can be ring-shaped. Optionally, the collar 500 can have two opposing ends that couple together to form the ring shape. For example, the collar 500 can comprise a protrusion 502 positioned at a first end 506 that is configured to be received into one or more holes 504 in an opposing second end 508. The protrusion 502 can have an enlarged distal end that has a diameter that is greater than the diameter of the one or more holes 504 so that once inserted into a hole, it cannot inadvertently fall out (due to engagement between the surfaces of the protrusion and the portion of the second end that defines the hole). It is contemplated that the one or more holes 504 can comprise a plurality of holes 504 spaced about the circumferences of the collar 500 so that the collar can have a selectable operative diameter, depending on the hole into which the protrusion 502 is inserted, in order to adapt the collar to differently sized test subjects.

Optionally, the collar 500 can have an inner surface 510 that is jagged, serrated, or toothed. Optionally, the collar 500 can have an outer surface 512 that is axially tapered. The collar 500 can be oriented so that the outer surface tapers in a direction away from the head of the test subject.

It is contemplated that both excessive weight of the collar and sound reflection can reduce the life of the test subject. Accordingly, in some aspects, the collar 500 can define a plurality of holes 514 that can optionally extend axially therethrough (through the thickness of the collar). The holes 514 can reduce the amount of material, and thus, the weight of the collar as well as minimize sound reflection that can cause stress to the test subject.

The collar 500 can optionally be flexible. Optionally, the collar can comprise polymer, such as, for example, silicone.

The Swivel Assembly

Figure 12B:
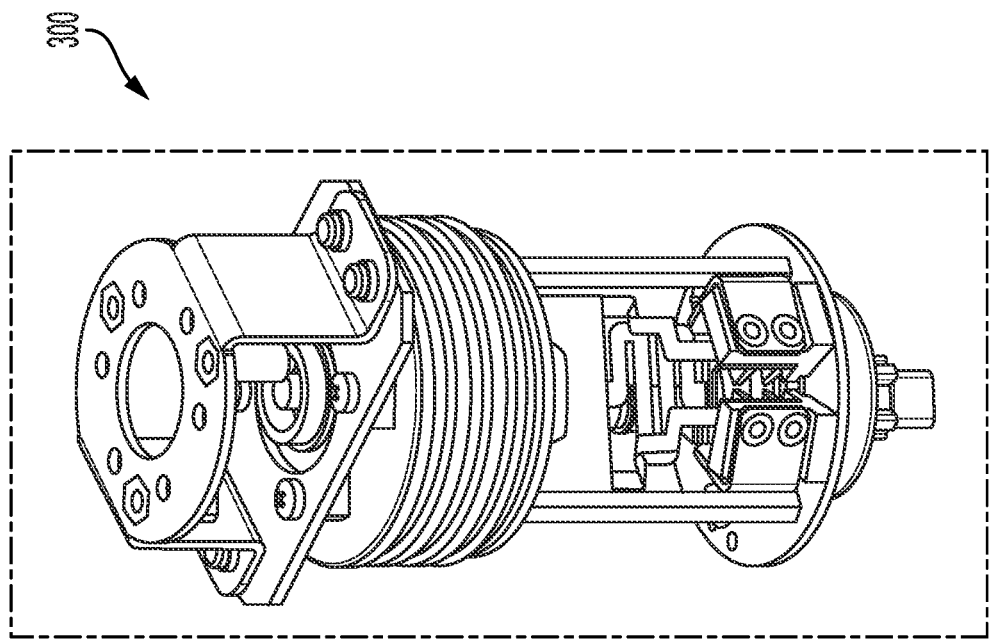
FIG. 12B is a detail view of the swivel of FIG. 12A.
Figure 12A:
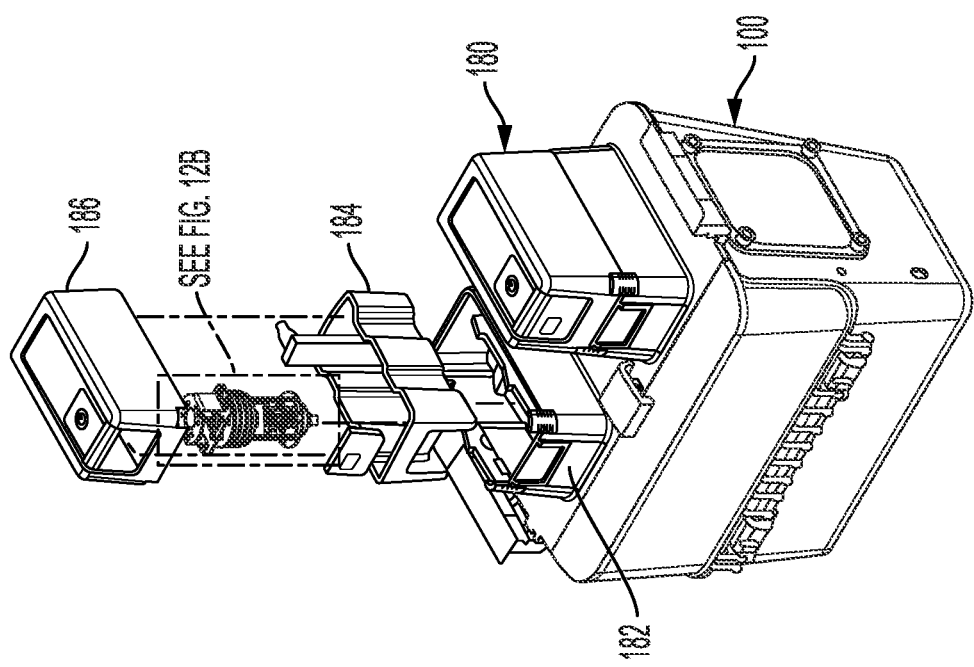
FIG. 12A is a partially exploded view of a cage, showing positioning of a swivel in relation to an associated cage assembly in accordance with embodiments disclosed herein.
Figure 14:
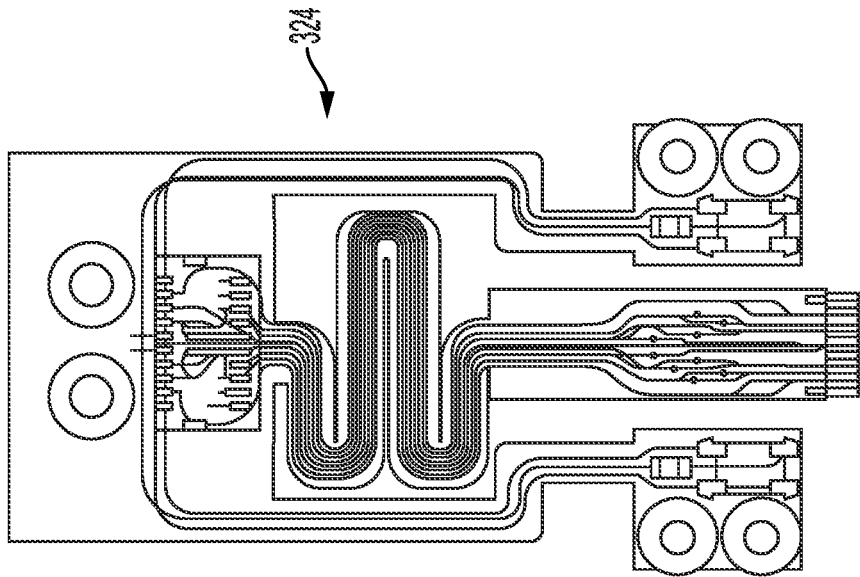
FIG. 14 is transparent view of the circuit board of FIG. 13 showing the inner circuitry.
Figure 15:
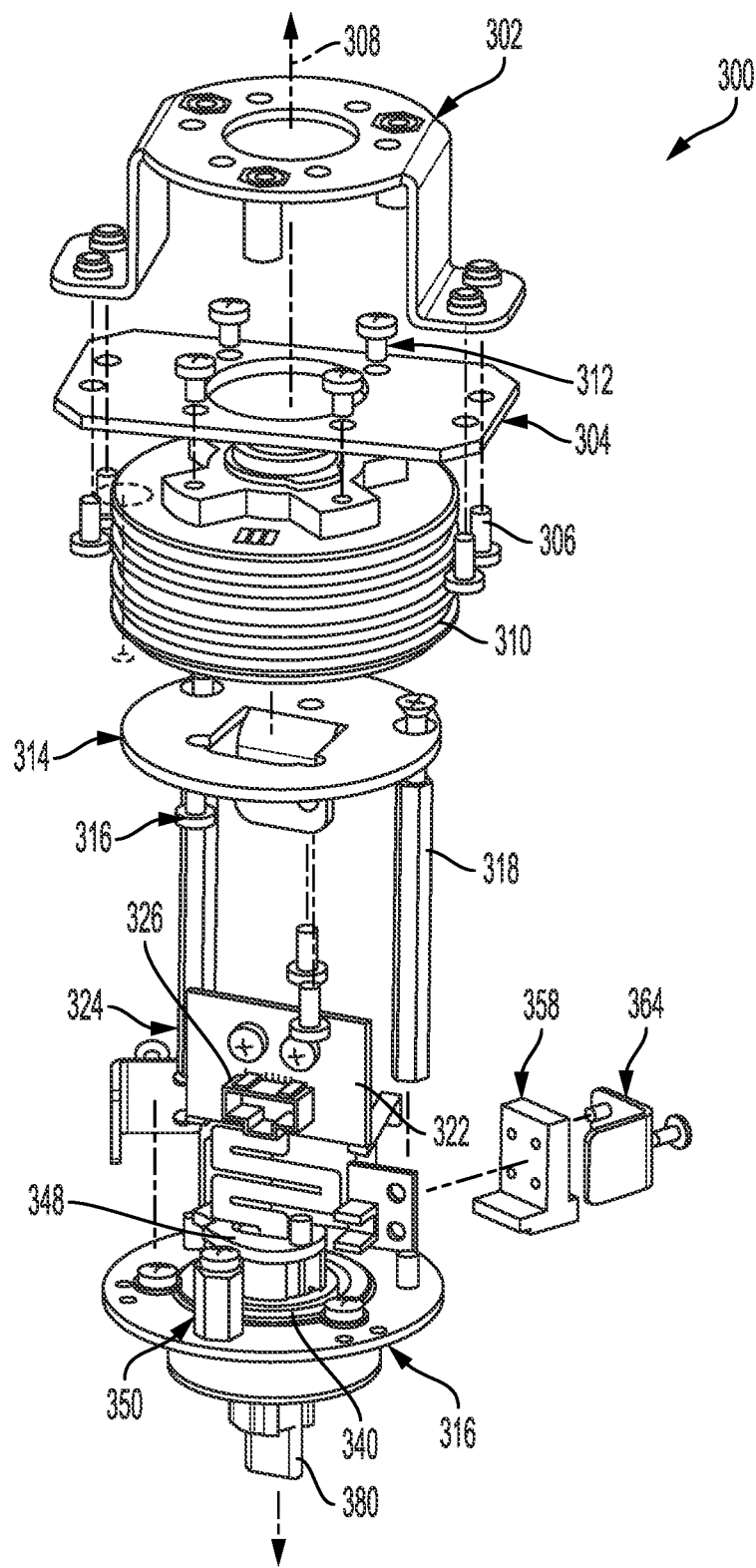
FIG. 15 is an exploded view of the swivel of FIG. 12B.
Figure 16:
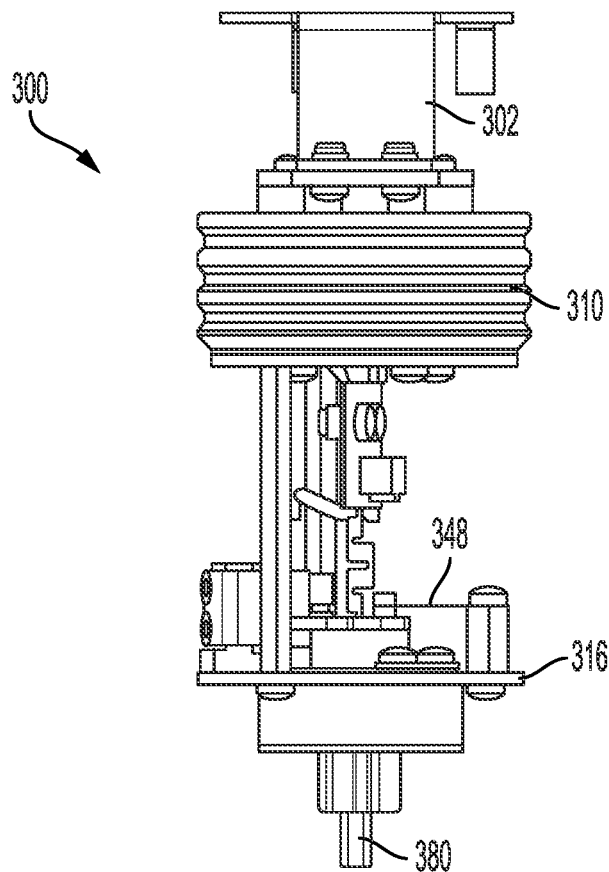
FIG. 16 is a side view of the swivel of FIG. 12B.
Figure 17:
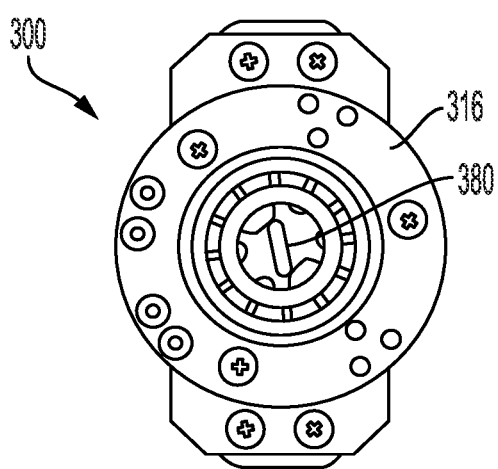
FIG. 17 is an underside view of the swivel of FIG. 12B.

Referring to FIGS. 12 and 15, the swivel 300 can be mounted to the cover 120 within the swivel housing 180. The swivel housing 180 can comprise a sidewall 182 that is integral to the cover 120. The swivel housing 180 can receive a removable inner circumferential insert 184. The swivel housing can further comprise a top cover 186 that couples to the sidewall 182.

The swivel 300 can comprise a damper plate 302 that attaches to the top cover 186 via screws or other fasteners. The top cover 186 can be a part of the swivel module. The damper plate 302 can couple to a motor mounting plate 304 via screws 306. The swivel 300 can have a central axis 308, and the motor 310 can rotate about the central axis 308. A motor 310 can couple to the motor mounting plate 306 via screws 312. A rotatable base 314 can attach to the motor 310 via screws 316. Thus, the rotatable base can be rotatable with respect to the motor mounting plate 304 via the motor. A bearing housing 316 can couple to the rotatable base 314 via standoffs 318. The rotatable base 314 can define a depending tab 320 that can couple to a flexible circuit assembly 322.

In some optional aspects, the top cover 186 can comprise at least one input device (e.g., a button) that is configured to start and stop therapy (e.g., TTField or heat). Optionally, the at least one input device can comprise a plurality of input devices, with each input device being configured to control operation of a different component of the system. In some aspects, respective input devices can be configured to control TTField application and heat application. In further aspects, an input device can be configured to start and stop operation of the swivel. In further aspects, the top cover 186 can comprise a display that is configured to show information, such as, for example, experiment identification information (e.g., cage number, electrode type) or an operation mode (e.g., idle, therapy, heat, pause). In various aspects, the top cover 186 can provide a communication port that can be in communication with the swivel 300 to provide communication between the signal generator 12 (FIG. 1) and a treatment/control heater assembly.

Figure 13:
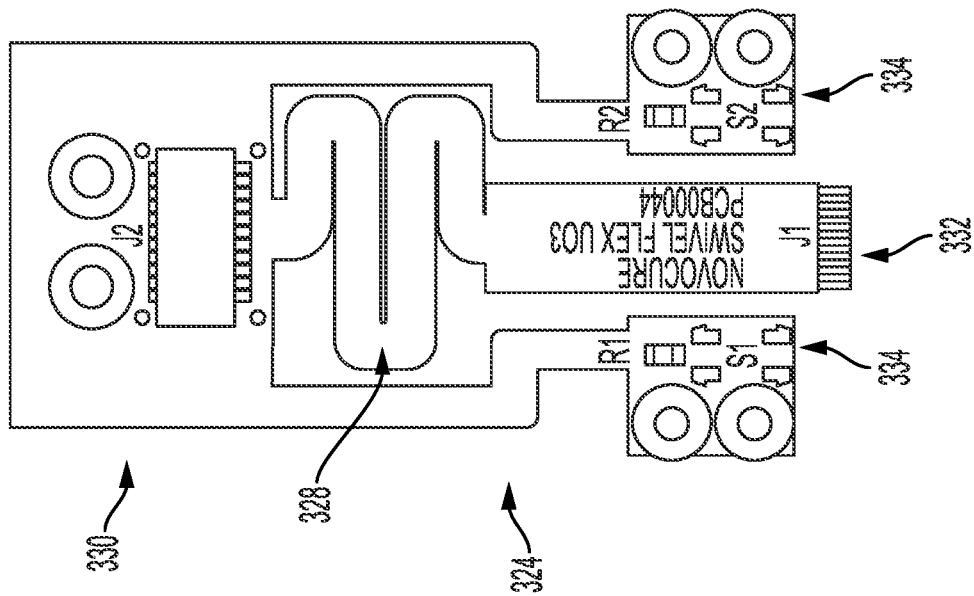
FIG. 13 is a side view of a circuit board of the swivel assembly of FIG. 12B.

Referring also to FIGS. 13 and 15, the flexible circuit assembly 322 can comprise a printed circuit board (PCB) 324 having an input/output connector 326 attached thereto. The connector 326 can provide communication to the upper portion of the swivel. The printed circuit board 324 can define a patterned portion 328 that extends between a base portion 330 and a cable connector end 332. The patterned portion 328 can have a structure that enables the printed circuit board 324 to twist so that the connector end 332 can pivot with respect to the base portion 330, as further described herein. In exemplary aspects, the patterned portion 328 can have a serpentine, wavelike, zig-zag, or undulating pattern. A pair of sensor connector portions 334 can extend from the base portion 330.

Referring also to FIGS. 18A,B and 19, the bearing housing 316 can house a bearing 340 (e.g., a ball bearing or a nylon bearing) that can receive and support a pivot body 342 within its inner race. The pivot body 342 can define a slot 344 therein that can receive the connector end 332 of the printed circuit board 324. The slot 344 can receive and engage the connector end 332 so that as the connector end pivots about the central axis 308, the pivot body can correspondingly pivot. (Although the Figures show the connector end 332 remaining in place as the pivot body pivots, it should be understood that, in use, the connector end pivots with the pivot body.) The pivot body 342 can define a cantilevered tab 346 that extends parallel to the central axis 308.

A centralizing spring 348 can extend from a standoff 350 that is attached to the bearing housing 316 to engage a protrusion 352 or other radially extending surface that is spaced from or extends away from the central axis 308 of the swivel 300. The centralizing spring 348 can bias the pivot body 316 to a neutral position 354. In use, when the printed circuit board 324 is under no or substantially no torque, then the pivot body can be in the neutral position 354.

Figure 23:
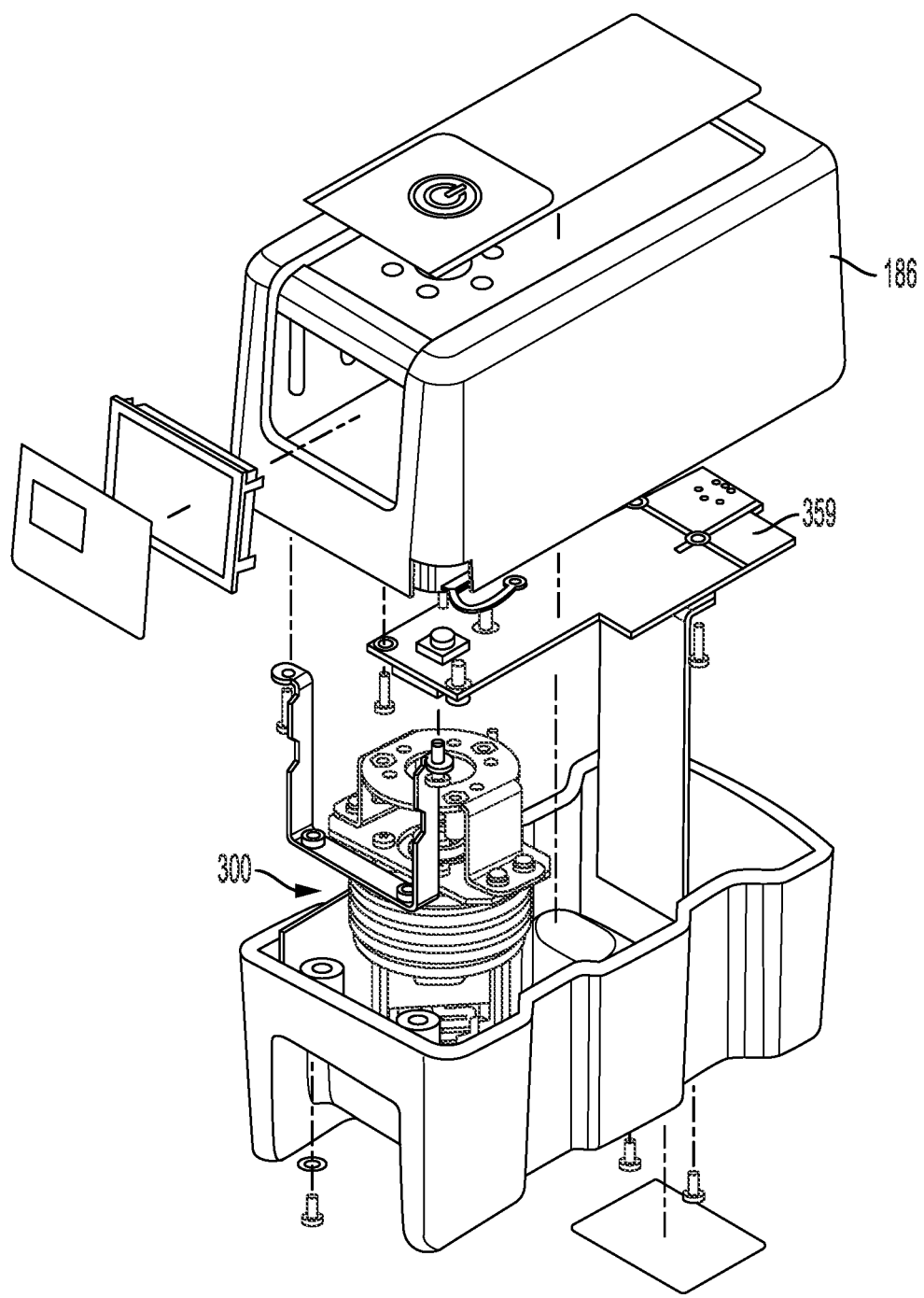
FIG. 23 is an exploded view of an embodiment of the swivel and its housing.

Referring to FIGS. 15, 18A,B, and 19, a pair of sensors 356 (e.g., electro-optical sensors, such as, for example, VISHAY TCPT1600X01 sensors) can attach to the bearing housing 316 via respective sensor mounts 358. The sensors 356 can be in communication with the PCB 324 at the sensor connector portions 334. The sensors 356 can be in communication with a processor (e.g., a PLC controller on a circuit board 359, as shown in FIG. 23). The sensors can have a light source, a photodetector, and a light path between the light source and the photodetector. The sensors 356 can be positioned so that when the pivot body 316 is in the neutral position, the cantilevered tab 346 can block both of the sensors 356. The test subject, as it walks within the cage, can twist the cable 204 (FIG. 8), thereby applying a torsion to the pivot body 342 and causing the pivot body to pivot from its neutral position. When the pivot body pivots sufficiently from the neutral position 350 in a first direction 360 (see FIG. 19), the cantilevered tab 346 can be outside of the light path of a first sensor 356A, and the first sensor can detect light from the light source in the photodetector. In this way, the swivel 300 can detect a twist of the cable in the first direction. The processor can cause the motor 310 to rotate in the first direction 360 to relieve the torsion on the cable. Optionally, the swivel can be configured to remain stationary until a minimum threshold angle from the neutral position 350 is reached in order to prevent excessive movement that can cause wear on the motor. Optionally, the motor can rotate a minimum angular distance in order to minimize excessive numbers of small movements. Likewise, when the pivot body pivots sufficiently from the neutral position 350 in a second direction 362 (opposite the first direction), a second optic sensor 356B can detect such a condition, and the processor can cause the motor to rotate in the second direction to relieve the torsion on the cable. In this way, the swivel can limit the amount of twisting in the cable 204 to thereby allow free movement of the test subject within the cage.

A limiter 364 can attach to each sensor mount 358. Each limiter 364 can comprise a centrally extending portion that can act as a stop to prevent the pivot body from pivoting more than a threshold angle from the neutral position 350, thereby preventing the printed circuit board 324 from breaking.

The pivot body 342 can define a connector 380 that is configured to receive the connector end 206,206', 406,406' of the flexible circuit board and electrically couple the flexible circuit board to the PCB 332. For example, the connector 380 can comprise a USB-C connector that is complementary to the connector end of the flexible circuit board (e.g., a female USB-C connector). Optionally, the connector 380 can comprise a CAN bus connection.

The swivel can comprise a slip ring that can maintain electrical communication through the swivel to thereby enable communication between the treatment assemblies 200 (or treatment assemblies 200' or treatment assemblies 200"), heater assemblies 400, or heater assemblies 400') and the TTFields generator 18. The slip ring can enable communication of at least twenty communication channels.

The computing device 1001 can be in communication with the swivel 300 (e.g., through cable 20 or another cable) in order to track and/or log various metrics. In further aspects, the computing device 1001 can be embodied as the controller on the PCB 359 (FIG. 23). For example, the metrics can include some or all of the following metrics: a number of rotations, a number of rotations in a first select duration, a frequency of motor movements, a frequency of motor movements in a second select duration, a number of motor movements comprising a change in direction, a number of motor movements in a third select duration comprising a change in direction, a duration of constant movement, and a log of motor movements and the corresponding time of the motor movements. Such metrics can be indicative of abnormal behavior in the test subjects. Further, such metrics can be indicative of malfunctioning of the swivel 300. In some aspects, a warning (e.g., a warning light or audible alarm) can be activated to notify a user that the swivel 300 is malfunctioning or the test subject is behaving abnormally. In further aspects, the computing device or controller in communication with the swivel can be configured to receive a user input. The user input can define one or more thresholds, such as, for example, a frequency threshold (e.g., a frequency of changes in direction of rotation) or a time threshold (e.g., a duration of constant rotation threshold). Upon exceeding the respective thresholds, the warning can be activated.

In further aspects, the computing device can generate and output a log report comprising at least one of the metrics that is collected. The log report can further output a comparison of the metrics based on comparisons to average metrics. The average metrics can be the average metrics for similar test subjects or for average metrics for a given subject over a select time period (e.g., over the course of an hour, a day, or a week). For example, the average metrics can comprise an average amount of movement that the test subject moves each day. Thus, it is contemplated that a decreasing amount of movement each day can be indicative of degrading health of the test subject. It is further contemplated that an excessively high amount of movement or an excessively low amount of movement in comparison to other similar test subjects can indicate relative health of the test subject. It is further contemplated that the monitoring of various metrics can allow for identification of modifications to ensure that animal subjects survive through the end of an experimental period.

Referring to FIG. 1, a plurality of test subjects 12 of an experimental group 14 can be fitted with a respective treatment assembly. The treatment assembly can be selected to treat the particular tumor (e.g., a treatment assembly 200 for an organ tumor or a treatment assembly 200' for a subcutaneous tumor). The treatment assembly can be properly sized. For example, for the organ tumor, the longitudinal length of the treatment assembly can be suitable to snugly wrap around the girth of the torso of the test subject along the torso at the given tumor. For a subcutaneous tumor, the through hole and cap of the treatment assembly can be selected to fit the subcutaneous tumor with minimal excess space. The length of the cable of the treatment assembly can be selected, as disclosed herein, to enable the test subject to freely travel the floor area of the enclosure while not providing excess length that can enable tangling. The release liner can be removed to allow the adhesive to engage the test subject's skin. The test subject's fur can be removed at the application area with a trimming device and/or a hair removal cream (e.g., VEET hair removal cream). Similarly, test subjects 12 of the control group can be fitted with respective control heater treatment assemblies 400 or control heater treatment assemblies 400' (to match the experimental group's counterpart).

The treatment assembly can be positioned on the body so that the electrodes are positioned as close as possible to the tumor. In various aspects, the treatment assembly (or control heater assembly) can be positioned on the body of the test subject so as to minimize or eliminate interruption of natural movements. For example, if the treatment assembly can be positioned away from the hind legs or the front legs of a mouse to allow natural movements. The treatment assembly can be selected based at least in part on the size of the mouse. For example, a narrow treatment assembly can be positioned on a mouse weighing less than 23 grams, and a wide treatment assembly can be positioned on a mouse weighing greater than 23 grams.

The treatment array (or control heater assembly) can be oriented so that the cable extends toward the tail/hind end of the test subject. It is contemplated that the subcutaneous treatment assembly and control heater assemblies can have formed bends (e.g., 90 degree bends) that can enable the cable to extend to the middle of the back of the test subject and then extend along the back toward the hind end. The formed bends can be provided in either direction, depending on the side of the test subjection on which the subcutaneous tumor is positioned. An adhesive (e.g., plaster) can be disposed on the test subject to promote adherence of the treatment assembly (or control heater assembly).

The test subjects can be placed within respective enclosures of cage assemblies. The connector end of each treatment assembly and control heater treatment assembly 400 can be attached to a respective swivel.

Figure 20:
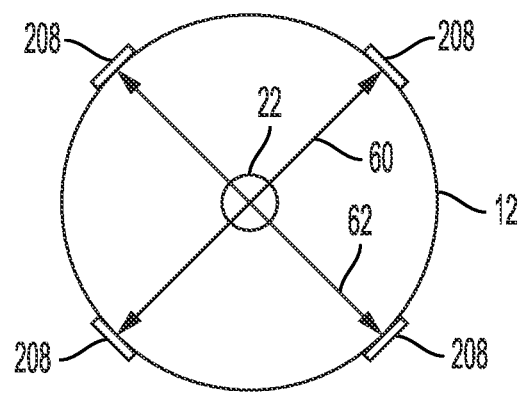
FIG. 20 is a schematic of a treatment assembly, in accordance with embodiments disclosed herein, for providing treatment to an organ tumor.
Figure 21:
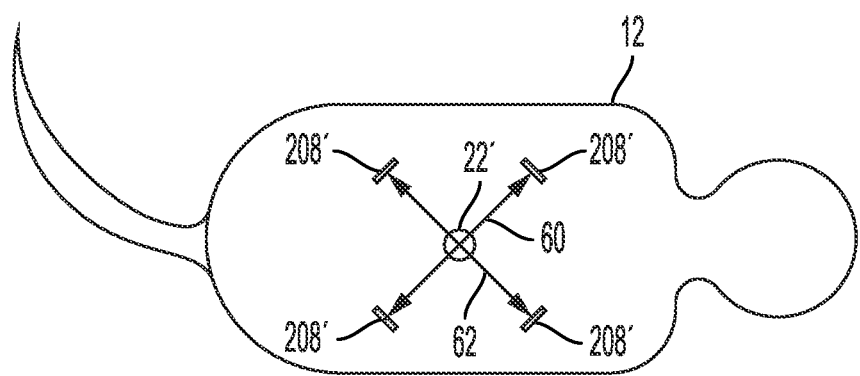
FIG. 21 is a schematic of a treatment assembly, in accordance with embodiments disclosed herein, for providing treatment to a subcutaneous tumor.

The treatment assemblies can be controlled to provide TTFields to the test subjects. For example, referring to FIGS. 20 and 21, TTFields from 50-500 kHz (optionally, 150-500 kHz) can be delivered to an organ tumor 22 (FIG. 20) or a subcutaneous tumor 22' (FIG. 21). Optionally, the TTFields can be delivered sequentially in separate axes of propagation (to provide alternating fields). For example, a first pair of opposing electrodes can apply a first electric field across the tumor along a first axis of propagation 60. A second pair of electrodes that are positioned so as to have a second axis of propagation 62 that is perpendicular or substantially perpendicular to the first axis of propagation can alternate with the first pair of opposing electrodes to provide alternating fields across the tumor. For the treatment assembly 200, each electrode can cooperate with a respective electrode positioned farthest from its location (e.g., on the other side of the body of the test subject) to provide alternating TTFields. Optionally, each electrode can be independently controlled to provide a tailored treatment. The control heater treatment assemblies can be controlled via a TTField generator or other controller to provide placebo heat to match or substantially match the temperatures of the treatment assemblies. The treatments can optionally continue for about 1-2 weeks.

The tumors of the experimental group and the control group can be compared during and after treatment. For example, for subcutaneous tumors, while leaving the treatment assembly attached to the subject, the cap can be removed to expose the tumor, and the tumor size can be measured with calipers. Organ tumors can be measured via, for example, Magnetic Resonance Imaging (MRI), ultrasound (US), or computed tomography (CT) scans. The treatment assemblies can be removed prior to such scans.

Computing Device

Figure 22:
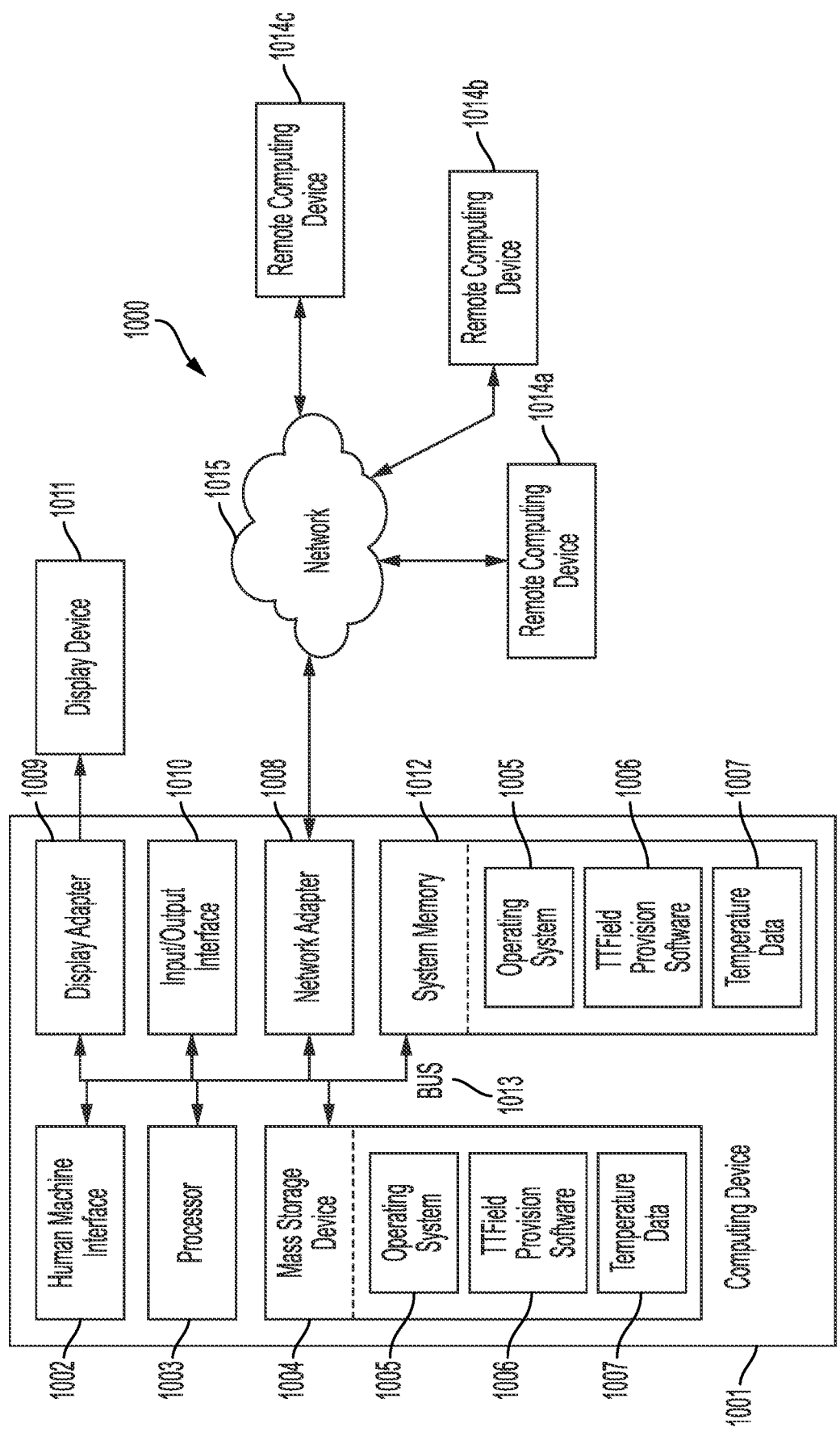
FIG. 22 is a schematic of a computing device for use with the system of FIG. 1.

FIG. 22 shows a system 1000 including an exemplary configuration of a computing device 1001 for use in the system 10.

The computing device 1001 may comprise one or more processors 1003, a system memory 1012, and a bus 1013 that couples various components of the computing device 1001 including the one or more processors 1003 to the system memory 1012. In the case of multiple processors 1003, the computing device 1001 may utilize parallel computing.

The bus 1013 may comprise one or more of several possible types of bus structures, such as a memory bus, memory controller, a peripheral bus, an accelerated graphics port, and a processor or local bus using any of a variety of bus architectures.

The computing device 1001 may operate on and/or comprise a variety of computer readable media (e.g., non-transitory). Computer readable media may be any available media that is accessible by the computing device 1001 and comprises, non-transitory, volatile and/or non-volatile media, removable and non-removable media. The system memory 1012 has computer readable media in the form of volatile memory, such as random access memory (RAM), and/or non-volatile memory, such as read only memory (ROM). The system memory 1012 may store data such as temperature data 1007 (i.e., data from signals received by the electrodes) and/or program modules such as operating system 1005 and TTField provision software 1006 that are accessible to and/or are operated on by the one or more processors 1003.

The computing device 1001 may also comprise other removable/non-removable, volatile/non-volatile computer storage media. The mass storage device 1004 may provide non-volatile storage of computer code, computer readable instructions, data structures, program modules, and other data for the computing device 1001. The mass storage device 1004 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 1004. An operating system 1005 and TTField provision software 1006 may be stored on the mass storage device 1004. One or more of the operating system 1005 and TTField provision software 1006 (or some combination thereof) may comprise program modules and the TTField provision software 1006. Temperature data 1007 may also be stored on the mass storage device 1004. Temperature data 1007 may be stored in any of one or more databases known in the art. The databases may be centralized or distributed across multiple locations within the network 1015.

A user may enter commands and information into the computing device 1001 using an input device (not shown). Such input devices comprise, but are not limited to, a keyboard, pointing device (e.g., a computer mouse, remote control), a microphone, a joystick, a scanner, tactile input devices such as gloves, and other body coverings, motion sensor, and the like. These and other input devices may be connected to the one or more processors 1003 using a human machine interface 1002 that is coupled to the bus 1013, but may be connected by other interface and bus structures, such as a parallel port, game port, an IEEE 1394 Port (also known as a Firewire port), a serial port, network adapter 1008, and/or a universal serial bus (USB).

A display device 1011 may also be connected to the bus 1013 using an interface, such as a display adapter 1009. It is contemplated that the computing device 1001 may have more than one display adapter 1009 and the computing device 1001 may have more than one display device 1011. A display device 1011 may be a monitor, an LCD (Liquid Crystal Display), light emitting diode (LED) display, television, smart lens, smart glass, and/or a projector. In addition to the display device 1011, other output peripheral devices may comprise components such as speakers (not shown) and a printer (not shown) which may be connected to the computing device 1001 using Input/Output Interface 1010. Any step and/or result of the methods may be output (or caused to be output) in any form to an output device. Such output may be any form of visual representation, including, but not limited to, textual, graphical, animation, audio, tactile, and the like. The display 1011 and computing device 1001 may be part of one device, or separate devices.

The computing device 1001 may operate in a networked environment using logical connections to one or more remote computing devices 1014a,b,c. A remote computing device 1014a,b,c may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computing device 1001 and a remote computing device 1014a,b,c may be made using a network 1015, such as a local area network (LAN) and/or a general wide area network (WAN). Such network connections may be through a network adapter 1008. A network adapter 1008 may be implemented in both wired and wireless environments. Such networking environments are conventional and commonplace in dwellings, offices, enterprise-wide computer networks, intranets, and the Internet. It is contemplated that the remote computing devices 1014a,b,c can optionally have some or all of the components disclosed as being part of computing device 1001.

Application programs and other executable program components such as the operating system 1005 are shown herein as discrete blocks, although it is recognized that such programs and components may reside at various times in different storage components of the computing device 1001, and are executed by the one or more processors 1003 of the computing device 1001. An implementation of electrode data processing software 1006 may be stored on or sent across some form of computer readable media. Any of the disclosed methods may be performed by processor-executable instructions embodied on computer readable media.

EXEMPLARY ASPECTS

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1A: A cage assembly comprising: at least one enclosure, each enclosure having: a floor defining a floor area having a major dimension; a cover having a bottom surface, wherein a spacing between the bottom surface of the cover and the floor defines a cage height; and at least one sidewall extending between the floor and the cover, wherein a ratio of the cage height to the major dimension of the floor area of each enclosure of the at least one enclosure is at least 0.70.

Aspect 2A: The cage assembly of aspect 1A, wherein the at least one enclosure comprises first and second enclosures.

Aspect 3A: The cage assembly of aspect 1A, wherein the at least one enclosure consists of first and second enclosures.

Aspect 4A: The cage assembly of aspect 2A or aspect 3A, wherein the first and second enclosures share a common sidewall that separates the floor area of the first enclosure from the floor area of the second enclosure.

Aspect 5A: The cage assembly of aspect 4A, wherein the common sidewall defines at least one opening between the first enclosure and the second enclosure.

Aspect 6A: The cage assembly of aspect 5A, wherein each of the first and second enclosures comprises a respective shelter subassembly that extends inwardly from the common sidewall within the enclosure, and wherein the shelter subassembly at least partially surrounds the opening within the common sidewall.

Aspect 7A: The cage assembly of any one of the preceding aspects, wherein the floor of each enclosure defines corners, each corner of the floor of the enclosure having a radius of at least 17 mm.

Aspect 8A: The cage assembly of any one of the preceding aspects, wherein the major dimension of the floor area of each enclosure is no greater than 250 mm.

Aspect 9A: The cage assembly of any one of aspects 2A-8A, wherein the floors of the first and second enclosures are unitarily constructed.

Aspect 10A: The cage assembly of any one of aspects 2A-9A, wherein the covers of the first and second enclosures are unitarily constructed as a cover assembly.

Aspect 11A: The cage assembly of aspect 10,A wherein the cover assembly comprises first and second openings that provide communication, respectively, with the first and second enclosures, wherein the first opening is configured provide communication for a first cable, and wherein the second opening is configured provide communication for a second cable.

Aspect 12A: The cage assembly of aspect 11A, wherein the cover assembly comprises first and second swivel assemblies positioned in overlying relation, respectively, to the first and second openings, wherein the first swivel assembly is configured to receive a proximal portion of the first cable, and wherein the second swivel assembly is configured to receive a proximal portion of the second cable.

Aspect 13A: The cage assembly of aspect 12A, wherein each of the first swivel assembly and the second swivel assembly comprises a motor housing and a motor received within the motor housing, wherein the motor of the first swivel assembly is configured to be coupled to a first cable to permit adjustment of the first cable, and wherein the motor of the second swivel assembly is configured to be coupled to a second cable to permit adjustment of the second cable.

Aspect 14A: The cage assembly of aspect 1A, wherein the at least one enclosure comprises a first enclosure, wherein the cover comprises a swivel assembly positioned in overlying relation to the first enclosure, wherein the cover further comprises an opening that provides communication with the first enclosure, wherein the opening is configured to provide communication between the cable and the swivel assembly.

Aspect 15A: The cage assembly of aspect 14A, wherein the swivel assembly comprises a motor, wherein the motor is configured to be coupled to a proximal portion of the cable to permit adjustment of movement of the cable.

Aspect 16A: The cage assembly of any one of aspects 4A-13A, wherein the at least one sidewall of each of the first and second enclosures further comprises: a front sidewall; a rear sidewall; and a transverse sidewall opposing the common sidewall and extending between the front sidewall and the rear sidewall.

Aspect 17A: The cage assembly of aspect 16A, wherein at least a portion of the front sidewalls of the first and second enclosures are unitarily constructed.

Aspect 18A: The cage assembly of aspect 16A or aspect 17A, wherein the rear sidewalls of the first and second enclosures are unitarily constructed.

Aspect 19A: The cage assembly of aspect 17A, wherein the front sidewalls of the first and second enclosures comprise: a base portion that is secured to the transverse sidewalls of the first and second enclosures; and a door that is pivotably coupled to the base portion, wherein the door is configured for movement about and between a closed position in which the door cooperates with the front, transverse, and rear sidewalls and the covers of the first and second enclosures to enclose an interior space within the cage assembly and an open position in which the interior space of the cage assembly is accessible.

Aspect 20A: The cage assembly of aspect 19A, wherein the door is pivotably coupled to the base portion by a hinged connection.

Aspect 21A: The cage assembly of aspect 19A or aspect 20A, further comprising a latch that is mechanically coupled to the door, wherein the latch is moveable about and between a latched position that prevents pivotal movement of the door when the door is in the closed position and an unlatched position that permits pivotal movement of the door relative to the base portion.

Aspect 22A: The cage assembly of any one of the preceding aspects, wherein the floor, the cover, and the at least one sidewall of each enclosure comprise polycarbonate.

Aspect 23A: The cage assembly of any one of the preceding aspects, wherein at least a portion of the cover and the at least one sidewall of each enclosure are transparent.

Aspect 24A: The cage assembly of any one of the preceding aspects, wherein the cover defines an opening that is configured to receive an electrical cord.

Aspect 25A: The cage assembly of any one of the preceding aspects, wherein the floor of each enclosure comprises padding.

Aspect 26A: The cage assembly of any one of the preceding aspects, wherein at least one sidewall of each enclosure comprises ventilation openings.

Aspect 27A: The cage assembly of aspect 26A, further comprising at least one filter that is configured to overlie at least one ventilation opening of the at least one sidewall.

Aspect 28A: The cage assembly of aspect 27A, further comprising a frame that is configured to mechanically couple the filter to the at least one sidewall.

Aspect 29A: The cage assembly of aspect 27A, wherein the cage assembly is sealed so that all or substantially all ventilation to each enclosure travels through the at least one filter before entering a ventilation opening.

Aspect 30A: The cage assembly of any one of the preceding aspects, wherein the sidewalls of each enclosure have equal lengths.

Aspect 31A: The cage assembly of any one of the preceding aspects, wherein the ratio of the cage height to the major dimension of the floor area of each enclosure of the at least one enclosure is at least 1.0.

Aspect 32A: A cage assembly comprising: at least one enclosure, each enclosure having: a floor defining floor area having a major dimension; a cover having a bottom surface, wherein a spacing between the bottom surface of the cover and the floor defines a cage height; and at least one sidewall extending between the floor and the cover, wherein the height, h, is a function of the major dimension, Y, of the floor according to the formula: $h \geq (Y2-6400)/320$, where h and Y are in millimeters.

Aspect 33A: A method comprising: positioning an animal subject within each enclosure of the cage assembly of any one of the preceding aspects; and coupling a distal end of a cable to the animal subject within each enclosure, wherein at least 90% of the floor area of the enclosure is accessible by the animal subject.

Aspect 34A: The method of aspect 33, further comprising: coupling a proximal end of each cable to a swivel assembly, wherein each cable has an operative portion having an operative length, wherein each operative length is selected so that each test subject can be at no position within a respective enclosure at which a spacing between the operative portion of the cable is within a threshold distance of the floor.

Aspect 35A: The method of aspect 33A or aspect 34A, wherein the animal subject is a mouse.

Aspect 36A: The method of aspect 35A, wherein the cage assembly comprises first and second enclosures, wherein a first mouse is positioned within the first enclosure, and wherein a second mouse is positioned within the second enclosure.

Aspect 37A: The method of aspect 36A, wherein the first and second enclosures share a common sidewall that separates the floor area of the first enclosure from the floor area of the second enclosure, wherein the common sidewall defines at least one opening between the first enclosure and the second enclosure, and wherein the at least one opening permits communication between the first mouse and the second mouse.

Aspect 38A: The method of any one of aspects 33A-37A wherein the electrical cord is coupled to the animal subject through a treatment assembly comprising a transducer array.

Aspect 39A: The method of aspect 38A, further comprising using the electrical cord and the treatment assembly to apply an electric field to the animal subject within at least one enclosure.

Aspect 40A: The method of aspect 39A, wherein the animal subject has a tumor, and wherein the electric field is a tumor-treating field.

Aspect 41A: The method of any one of aspects 33A-40A, further comprising inspecting or accessing the animal subject through the cage assembly without removing the animal subject from the cage assembly.

Aspect 42A: The method of any one of aspects 33A-41A, further comprising: removing the animal subject from the cage assembly; and autoclaving the floor, the cover, and the at least one sidewall of each enclosure.

Aspect 1B: A treatment assembly comprising: an inner layer having an inner surface and an outer surface, wherein the inner layer defines a plurality of openings extending therethrough; a plurality of plates, each plate being at least partially received within a respective opening of the plurality of openings of the inner layer; treatment circuitry comprising: a cable comprising having a plurality of electrical leads; and a plurality of electrical lead ends, each electrical lead being electrically connected to a respective electrical lead end of the plurality of electrical lead ends; and a cover layer attached to the outer surface of the inner layer and overlying the plurality of electrical lead ends of the cable, wherein the plurality of lead ends are in contact with respective plates of the plurality of plates to define a plurality of electrodes, each electrode of the plurality of electrodes comprising a respective lead end and a respective plate.

Aspect 2B: The treatment assembly of aspect 1B, wherein at least one plate of the plurality of plates comprises a ceramic plate.

Aspect 3B: The treatment assembly of aspect 1B, wherein at least one plate of the plurality of plates comprises a glass plate.

Aspect 4B: The treatment assembly of any one of aspects 1B-3B, wherein at least one electrode of the plurality of electrodes is configured to generate an electric field through a corresponding plate of the plurality of plates.

Aspect 5B: The treatment assembly of any one aspects 1B-4B, wherein the plurality of electrodes of the treatment circuitry have respective top surfaces, and wherein the cover layer extends across the top surfaces of the electrodes of the cable.

Aspect 6B: The treatment assembly of any one of aspects 1B-5B, wherein each plate of the plurality of plates has a lower surface and an opposing upper surface, wherein the treatment assembly further comprises a layer of hydrogel on the lower surface of each plate of the plurality of plates.

Aspect 7B: The treatment assembly of any one of aspects 1B-6B, wherein the treatment circuitry further comprises at least one temperature sensor.

Aspect 8B: The treatment assembly of any one of aspects 1B-7B, wherein the inner layer and the cover layer cooperate to define a hole through the treatment assembly, wherein the hole is configured to receive a subcutaneous tumor therethrough.

Aspect 9B: The treatment assembly of aspect 8B, further comprising a cap that extends across the hole and defines a receptacle therein that is configured to receive the subcutaneous tumor, wherein the cap is attached to the cover layer.

Aspect 10B: The treatment assembly of aspect 8B or aspect 9B, wherein the plurality of plates are positioned radially outwardly of the hole defined through the treatment assembly.

Aspect 11B: The treatment assembly of aspect 9B or aspect 10B, wherein the cap comprises a peripheral rim, and wherein the treatment assembly further comprises an adhesive ring that overlies the peripheral rim and secures the cap to the cover layer.

Aspect 12B: The treatment assembly of any one of aspects 1B-11B, wherein the treatment assembly has a longitudinal dimension in a pre-use configuration, wherein the cover layer comprises a biocompatible non-woven adhesive, wherein the non-woven adhesive is elastic in the longitudinal dimension.

Aspect 13B: The treatment assembly of aspect 12B, wherein in a use configuration, the cable extends perpendicularly or substantially perpendicularly relative to the longitudinal dimension.

Aspect 14B: The treatment assembly of any one of aspects 1B-13B, wherein the inner layer comprises a biocompatible breathable polyurethane adhesive on the inner surface of the inner layer.

Aspect 15B: The treatment assembly of aspect 14B, wherein the cover layer has an inner surface that comprises a biocompatible non-woven adhesive.

Aspect 16B: The treatment assembly of any one of aspects 1B-15B, wherein the plurality of electrodes comprises a plurality of electric field-generating electrodes, wherein the plurality of electric field-generating electrodes are configured to transmit an electric field through corresponding plates of the plurality of plates.

Aspect 17B: The treatment assembly of aspect 16B, wherein the treatment circuitry further comprises a plurality of thermistors.

Aspect 18B: The treatment assembly of aspect 17B, wherein a respective electrode of the plurality of electrodes and a respective thermistor of the plurality of thermistors is in communication with each plate of the plurality of plates.

Aspect 19B: The treatment assembly of any one of aspects 1B-18B, wherein the treatment assembly weighs less than 2.5 grams.

Aspect 20B: The treatment assembly of any one of aspects 1B-19B, wherein the treatment assembly is sufficiently flexible to circumferentially conform to a portion of a torso of the animal subject.

Aspect 21B: The treatment assembly of any one of aspects 1B-20B, wherein the cable comprises an end connector positioned on an end of the cable opposite the plurality of electrodes, wherein the end connector is configured to permit connection of the cable to an electrical signal generator.

Aspect 22B: The treatment assembly of aspect 14B, further comprising a release layer that contacts the biocompatible breathable polyurethane adhesive on the inner surface of the inner layer.

Aspect 23B: The treatment assembly of aspect 22B, wherein the release layer has a shape that is complementary to a shape of the cover layer.

Aspect 24B: The treatment assembly of any one of aspects 1B-23B, wherein the cover layer defines at least one tab portion that extends beyond the inner layer.

Aspect 25B: The treatment assembly of aspect 2B, wherein the at least one tab portion comprises two opposing tab portions that are complementary to one another when the cover layer defines a circumferential loop.

Aspect 26B: The treatment assembly of any one of aspects 1B-7B or aspects 12B-25B, wherein the plurality of openings comprises a plurality of longitudinally spaced openings.

Aspect 27B: The treatment assembly of any one of aspects 1B-26B, wherein the treatment circuitry and the cable are unitarily constructed as a flexible printed circuit board.

Aspect 28B: A method of making the treatment assembly of any one of aspects 1B-27B, the method comprising: positioning the plurality of plates within respective openings in the inner layer of the treatment assembly; positioning each electrode of the plurality of electrodes of the treatment circuitry in contact with a plate of the plurality of plates; and attaching the cover layer to the outer surface of the inner layer, wherein the cover layer overlies the plurality of electrodes of the treatment circuitry.

Aspect 29B: The method of aspect 28B, further comprising applying a layer of hydrogel to lower surfaces of each plate of the plurality of plates.

Aspect 30B: The method of aspect 29B, wherein the lower surfaces of at least two plates of the plurality of plates share a layer of hydrogel.

Aspect 31B: A method comprising: electrically coupling at least a portion of the electrodes of the treatment assembly of any one of aspects 1B-27B to an electrical signal generator; attaching the treatment assembly to an animal subject having a tumor, wherein the plates of the treatment assembly surround at least a portion of the tumor; and using the electrical signal generator to generate an electrical signal; and using said at least a portion of the electrodes of the treatment assembly to generate, from the electrical signal, an electric field through corresponding plates of the plurality of plates.

Aspect 32B: The method of aspect 31B, wherein the tumor is an organ tumor, wherein in a pre-use configuration, the plurality of openings and the plurality of plates are longitudinally spaced along a longitudinal axis of the treatment assembly, and wherein in a use configuration, the plurality openings and the plurality of plates are circumferentially spaced about a torso of the animal subject to surround the organ tumor.

Aspect 33B: The method of aspect 31B, wherein the tumor is a subcutaneous tumor, wherein the plurality of openings are radially spaced from a hole extending through the treatment assembly, and wherein the hole receives at least a portion of the subcutaneous tumor.

Aspect 34B: The method of aspect 33B, further comprising positioning a cap over the subcutaneous tumor and securing the cap to the cover layer of the treatment assembly.

Aspect 35B: The method of any one of aspects 31B-34B, wherein using the electrical signal generator to generate the electrical signal comprises sequentially generating first and second electrical signals, and wherein using said at least a portion of the electrodes of the treatment assembly to generate, from the electrical signal, the electric field comprises: using first and second electrodes to generate, from the first electrical signal, a first electric field across the tumor; and using third and fourth electrodes to generate, from the second electrical signal, a second electric field across the tumor.

Aspect 36B: The method of aspect 35B, wherein the first and second electric fields have respective axes of propagation, and wherein the axis of propagation of the first electric field intersects the axis of propagation of the second electric field.

Aspect 37B: The method of any one of aspects 28B-36B, wherein using the electrical signal generator to generate an electric field comprises generating the electric field at a frequency of between 50 and 500 kHz.

Aspect 38B: The method of any one of aspects 31B-37B, wherein the animal subject is a member of an experimental group, and wherein the method further comprises: electrically coupling at least a portion of the electrodes of a control heating device of any one of aspects 39B-42B to an electrical signal generator; attaching the control heating device to a second animal subject having a tumor, wherein the second animal subject is a member of a control group, wherein the heaters of the second treatment assembly surround at least a portion of the tumor; and using the electrical signal generator to generate heat through heaters of the control heating device, wherein the at least a portion of the electrodes of the second treatment assembly deliver the heat through corresponding plates of the plurality of plates, and wherein the heat generated by the control heating device simulates heat generated by the first treatment assembly during delivery of the electric field.

Aspect 39B: A control heating device comprising: circuitry comprising: a plurality of zones that are positioned in a spaced configuration that matches a configuration of the plurality of electrodes of the treatment assembly as in any of aspects 1B-27B, at least one heater positioned in each zone of the plurality of zones, at least one temperature sensor; and a cable in communication with the at least one heater and the at least one temperature sensor of the circuitry.

Aspect 40B: The control heating device of aspect 39B, wherein the at least one temperature sensor comprises a plurality of temperature sensors, wherein each temperature sensor of the plurality of temperature sensors is positioned at each zone of the plurality of zones.

Aspect 41B: The control heating device of aspect 39B or aspect 40B, wherein the circuitry and the cable are unitarily constructed as a flexible printed circuit board.

Aspect 42B: The control heating device of any one of aspects 39B-41B, further comprising an inner layer having an upper surface and comprising a plurality of openings, wherein each of the zones is disposed within an opening of the plurality of openings; and a cover layer extending across the upper surface of the inner layer.

Aspect 43B: The treatment assembly of any one of aspects 1B-27B, wherein the plurality of electrodes comprises a plurality of head electrodes that are configured to be positioned on a head of a test subject and a plurality of torso electrodes that are configured to be positioned on a torso of the test subject.

Aspect 44B: The treatment assembly of aspect 43B, wherein the treatment circuitry comprises a serpentine portion that extends from the plurality of torso electrodes to the plurality of head electrodes.

Aspect 45B: The treatment assembly of aspect 43B or aspect 44B, wherein the plurality of head electrodes comprises a first group of electrodes that are positioned on a first side relative to a medial plane and a second plurality of electrodes that are positioned on a second side, opposite the first side, relative to the medial plane, wherein the plurality of torso electrodes comprises at least a first torso electrode positioned on the first side and at least a second torso electrode positioned on the second side.

Aspect 1C: A swivel assembly having a longitudinal axis and comprising: an upper portion; a lower portion that is rotationally coupled to the upper portion, wherein the lower portion has a connector configured to securely engage a cable, wherein the lower portion is configured to remain in electrical communication with the upper portion as the lower portion rotates with respect to the upper portion; a motor disposed between the upper portion and the lower portion and configured to selectively rotate the lower portion; a sensor that is configured to detect torsion in the cable; and a controller in communication with the sensor and the motor, wherein, upon receiving a signal from the sensor indicating a threshold torsion in the cable, the controller is configured to cause the motor to rotate in a direction corresponding to a direction of the torsion in the cable.

Aspect 2C: The swivel assembly of aspect 1C, wherein the connector of the lower portion is an electrical connector, wherein the electrical connector is configured to securely engage an electrical cable.

Aspect 3C: The swivel assembly of aspect 2C, wherein the electrical connector is configured for electrical communication with an electrical signal generator, and wherein the electrical connector is further configured to permit electrical communication between the electrical signal generator and the electrical cable.

Aspect 4C: The swivel assembly of any one of aspects 1C-3C, wherein the controller is configured to cause the motor to rotate in the direction corresponding to the direction of a twist of the cable until the controller receives a signal from the sensor indicating that torsion in the cable has dropped below a second threshold.

Aspect 5C: The swivel assembly of any one of aspects 1C-4C, further comprising a mounting assembly attached to the upper portion of the swivel relative to the longitudinal axis, wherein the lower portion of the swivel is rotationally coupled to the mounting assembly via the upper portion of the swivel.

Aspect 6C: The swivel assembly of aspect 5C, wherein the mounting assembly is configured to be secured to a top surface of a cage.

Aspect 7C: The swivel assembly of aspect 5C or aspect 6C wherein the mounting assembly defines an opening in communication with the cable outlet.

Aspect 8C: The swivel assembly of any one of aspects 1C-7C, wherein the lower portion comprises a base plate that underlies and engages the motor, and wherein the motor imparts rotational force to the lower portion through the base plate.

Aspect 9C: The swivel assembly of any one of aspects 1C-8C, wherein the upper portion comprises a support plate that overlies the motor.

Aspect 10C: The swivel assembly of any one of aspects 1C-9C, wherein the upper portion further comprises a vibration-dampening plate that overlies the motor.

Aspect 11C: The swivel assembly of any one of aspects 1C-10C, wherein the controller is configured to detect abnormal rotation of the swivel assembly, wherein the abnormal rotation is detected by at least one of: (1) one or more signals from the sensor indicative of a frequency of a change in rotational direction that exceeds a frequency threshold; or (2) one or more signals from the sensor indicative of continuous rotation in a single direction that exceeds a time threshold.

Aspect 12C: The swivel assembly of aspect 11C, wherein the controller is configured to receive a user input to define at least one of the frequency threshold or the time threshold.

Aspect 13C: The swivel assembly of aspect 11C or aspect 12C, further comprising a warning indicator, wherein the controller is configured to activate the warning indicator upon detecting abnormal rotation.

Aspect 14C: The swivel assembly of aspect 13C, wherein the warning indicator comprises at least one of a visible indicator or an audible indicator.

Aspect 15C: The swivel assembly of any one of aspects 1C-14C, wherein the sensor is a torque sensor comprising: a pivot body that is pivotably coupled to the lower portion of the swivel about a pivot axis and is configured to be coupled to the cable so that torsion of the cable applies a torque to the pivot body that causes pivoting of the pivot body with respect to the lower portion of the swivel, wherein the pivot body comprises a radially extending surface that extends radially outwardly relative to the pivot axis; a spring that is configured to bias the pivot body to a neutral position with respect to the lower portion of the swivel; first and second electro-optical sensors that are radially spaced from the pivot axis of the pivot body and in respective angular positions with respect to the pivot body, wherein upon the pivot body pivoting a first threshold angular distance in a first direction from the neutral position, the radially-extending surface of the pivot body is configured to effect a change of state in the first electro-optical sensor, and wherein upon the pivot body pivoting a second threshold angular distance in an opposing second direction from the neutral position, the radially-extending surface of the pivot body is configured to effect a change of state in the second electro-optical sensor.

Aspect 16C: The swivel assembly of aspect 15C, further comprising a printed circuit board having a first portion that is rotationally fixed to the lower portion of the swivel, a second portion that is pivotable with the pivot body, and at least one cutout so that the printed circuit board comprises a patterned portion that enables the first portion to pivot with respect to the second portion.

Aspect 17C: The swivel assembly as in aspect 15C or aspect 16C, wherein each of the first and second electro-optical sensors comprises a light source, a photodetector, and a light path between the light source and the photodetector, wherein, when the pivot body is in the neutral position, the radially extending surface of the pivot body is configured to block the respective light path of each of the first electro-optical sensor and the second electro-optical sensor, wherein the change of state in the first electro-optical sensor upon the pivot body pivoting a first threshold angular distance in the first direction from the neutral position comprises the first electro-optical sensor no longer detecting the radially extending surface blocking the light path of the first electro-optical sensor.

Aspect 18C: The swivel assembly as in aspect 17C, wherein the radially extending surface of the pivot body comprises a protrusion.

Aspect 19C: The swivel assembly of any one of aspects 1C-18C, wherein the motor is a brushless gimbal motor.

Aspect 20C: The swivel assembly of any one of aspects 1C-19C, further comprising the cable, wherein the cable has a proximal end portion secured to the connector and an opposing distal end, wherein the cable is configured to move in response to application of force to the distal end portion of the cable.

Aspect 21C: The swivel assembly of any one of aspects 1C-20C, further comprising a slip ring that is configured to provide electrical communication between the upper portion and the lower portion as the lower portion rotates with respect to the upper portion.

Aspect 22C: The swivel assembly of any one of aspects 1C-21C, wherein the cable is a portion of a flexible printed circuit board.

Aspect 23C: A method comprising: securing a proximal end portion of a cable to the connector of the swivel assembly of any one of aspects 1C-22C; and in response to torsion in the cable in a first direction, using the controller to cause the motor to rotate in a direction corresponding to the first direction of the torsion of the cable.

Aspect 24C: The method of aspect 23C, wherein the cable is an electrical cable, and wherein the cable has a distal end portion that is electrically coupled to an electrode array.

Aspect 25C: The method of aspect 24C, wherein the electrode array is coupled to an animal subject.

Aspect 26C: The method of aspect 25C, wherein the animal subject is positioned within a cage, and wherein the swivel assembly is secured to the cage.

Aspect 27C: The method of any one of aspects 23C-26C, further comprising using the controller to determine an abnormal rotation based on at least one of the following: (1) one or more signals from the sensor indicative of a frequency of a change in rotational direction that exceeds a frequency threshold; or (2) one or more signals from the sensor indicative of continuous rotation in a single direction that exceeds a time threshold.

Aspect 28C: A system comprising: a swivel assembly as in any one of aspects 1C-22C; a computing device comprising a memory in communication with at least one processor, wherein the memory comprises instructions that, when executed, cause the at least one processor to perform a method comprising: storing in the memory at least one metric selected from the group consisting of: a number of rotations, a number of rotations in a first select duration, a frequency of motor movements, a frequency of motor movements in a second select duration, a number of motor movements comprising a change in direction, a number of motor movements in a second select duration comprising a change in direction, a duration of constant movement, and a log of motor movements and the corresponding time of the motor movements.

Aspect 29C: The swivel assembly of aspect 28C, wherein the memory comprises instructions that, when executed, cause the at least one processor to perform the method further comprising: generating a log report, wherein the log report comprises the at least one metric.

Aspect 30C: The swivel assembly of aspect 29C, wherein the log report further comprises at least one comparison of the at least one metric and an average of the at least one metric over a specified time.

Aspect 1D: A system comprising: a cage assembly of any one of aspects 1A-32A; and a swivel assembly of any one of aspects 1C-22C.

Aspect 2D: The system of aspect 1D, further comprising a treatment assembly of any one of aspects 1B-27B.

Aspect 3D: The system of aspect 1D, further comprising a control heating device of any one of aspects 39B-42B.

Aspect 4D: A method of using the system of any one of aspects 1D-3D.

Although the foregoing invention has been described in some detail by way of illustration and example for purposes of clarity of understanding, certain changes and modifications may be practiced within the scope of the appended claims.

What is claimed is:

1. A cage assembly comprising:
 at least one enclosure, each enclosure having:
  a floor defining a floor area having a major dimension;
  a cover having a bottom surface, wherein a spacing between the bottom surface of the cover and the floor defines a cage height; and
  at least one sidewall extending between the floor and the cover,
 wherein a ratio of the cage height to the major dimension of the floor area of each enclosure of the at least one enclosure is at least 0.70; and
 a first cable movably coupled to the cover of the at least one enclosure, the first cable having a predetermined operative length,
 wherein the cage height is selected to cooperate with the predetermined operative length of the first cable to maintain an entirety of the cable at or above a threshold distance from the floor of the at least one enclosure at every possible angular orientation of the first cable within the at least one enclosure, wherein the threshold distance is from 1 mm to 10 mm.

2. The cage assembly of claim 1, wherein the at least one enclosure comprises first and second enclosures, wherein the first and second enclosures share a common sidewall that separates the floor area of the first enclosure from the floor area of the second enclosure, wherein the common sidewall defines at least one opening between the first enclosure and the second enclosure.

3. The cage assembly of claim 1, wherein the floor of each enclosure defines corners, each corner of the floor of the enclosure having a radius of at least 17 mm.

4. The cage assembly of claim 1, wherein the major dimension of the floor area of each enclosure is no greater than 250 mm.

5. The cage assembly of claim 2, wherein the covers of the first and second enclosures are unitarily constructed as a cover assembly, wherein the cover assembly comprises first and second openings that provide communication, respectively, with the first and second enclosures, wherein the first opening is configured provide communication for the first cable, and wherein the second opening is configured provide communication for a second cable.

6. The cage assembly of claim 2, wherein the at least one sidewall of each of the first and second enclosures further comprises:
a front sidewall;
a rear sidewall; and
a transverse sidewall opposing the common sidewall and extending between the front sidewall and the rear sidewall.

7. The cage assembly of claim 6, wherein at least a portion of the front sidewalls of the first and second enclosures are unitarily constructed, and wherein the rear sidewalls of the first and second enclosures are unitarily constructed.

8. The cage assembly of claim 7, wherein the front sidewalls of the first and second enclosures comprise:
a base portion that is secured to the transverse sidewalls of the first and second enclosures; and
a door that is pivotably coupled to the base portion, wherein the door is configured for movement about and between a closed position in which the door cooperates with the front, transverse, and rear sidewalls and the covers of the first and second enclosures to enclose an interior space within the cage assembly and an open position in which the interior space of the cage assembly is accessible by exposing an opening at each enclosure of the first and second enclosures, wherein the door is pivotably coupled to the base portion by a hinged connection at an upper edge of the front sidewalls,
wherein the cage assembly further comprises a latch that is mechanically coupled to the door, wherein the latch is moveable about and between a latched position that prevents pivotal movement of the door when the door is in the closed position and an unlatched position that permits pivotal movement of the door relative to the base portion.

9. The cage assembly of claim 1, wherein the at least one sidewall defines one or more ventilation openings, wherein the cage assembly further comprises at least one filter that is configured to overlie at least one ventilation opening of the at least one sidewall, wherein the cage assembly is sealed so that all or substantially all ventilation to each enclosure travels through the at least one filter before entering a ventilation opening.

10. The cage assembly of claim 1, wherein the sidewalls of each enclosure have equal lengths.

11. The cage assembly of claim 1, wherein the ratio of the cage height to the major dimension of the floor area of each enclosure of the at least one enclosure is at least 1.0.

12. The cage assembly of claim 1, wherein the at least one enclosure comprises a first enclosure, wherein the cover comprises a swivel assembly positioned in overlying relation to the first enclosure, wherein a proximal end of the first cable is coupled to the swivel assembly, thereby coupling the first cable to the first enclosure, wherein the cover further comprises an opening that provides communication with the first enclosure, wherein the opening provides communication between the first cable and the swivel assembly.

13. The cage assembly of claim 12, wherein the swivel assembly comprises a motor, wherein the motor is configured to be coupled to a proximal portion of the cable to permit adjustment of movement of the cable.

14. A cage assembly comprising:
at least one enclosure, each enclosure having:
a floor defining a floor area having a major dimension;
a cover having a bottom surface, wherein a spacing between the bottom surface of the cover and the floor defines a cage height; and
at least one sidewall extending between the floor and the cover,
wherein the cage height, h, is a function of the major dimension, Y, of the floor area according to the formula: h≥(Y2−6400)/320, where h and Y are in millimeters; and
a first cable movably coupled to the cover of the at least one enclosure, the first cable having a predetermined operative length,
wherein the cage height is selected to cooperate with the predetermined operative length of the first cable to maintain an entirety of the cable at or above a threshold distance from the floor of the at least one enclosure at every possible angular orientation of the first cable within the at least one enclosure, wherein the threshold distance is from 1 mm to 10 mm.

15. A method comprising:
positioning an animal subject within each enclosure of a cage assembly, the cage assembly comprising:
at least one enclosure, each enclosure having:
a floor defining a floor area having a major dimension;
a cover having a bottom surface, wherein a spacing between the bottom surface of the cover and the floor defines a cage height; and
at least one sidewall extending between the floor and the cover,
wherein a ratio of the cage height to the major dimension of the floor area of each enclosure of the at least one enclosure is at least 0.70;
coupling a proximal end of each cable to a swivel assembly; and
coupling a distal end of a cable to the animal subject within each enclosure,
wherein each cable has an operative portion having an operative length, wherein each operative length is selected so that each animal subject can be at no position within a respective enclosure at which a spacing between any of the operative portion of the cable is within a threshold distance of the floor, and wherein at least 90% of the floor area of the enclosure is accessible by the animal subject.

16. The method of claim 15, further comprising: removing the animal subject from the cage assembly; and autoclaving the floor, the cover, and the at least one sidewall of each enclosure.

17. The method of claim 15, wherein the cable comprises an electrical cord that is coupled to the animal subject through a treatment assembly comprising a transducer array.

18. The method of claim 17, further comprising using the electrical cord and the treatment assembly to apply an electric field to the animal subject within at least one enclosure.

19. The cage assembly of claim 1, wherein the cage assembly comprises a treatment assembly that is configured to generate tumor-treating fields, wherein the treatment assembly comprises the first cable.

20. The cage assembly of claim 1, wherein the first cable extends from directly above a center of the floor space of a first enclosure of the at least one enclosure.

* * * * *